(12) United States Patent
Lee et al.

(10) Patent No.: US 11,540,380 B2
(45) Date of Patent: Dec. 27, 2022

(54) FLEXIBLE ACTIVE SPECIES GENERATOR AND USE THEREOF

(71) Applicant: KOREA INSTITUTE OF MACHINERY & MATERIALS, Daejeon (KR)

(72) Inventors: Seung Hoon Lee, Changwon-si (KR); Do Geun Kim, Changwon-si (KR); Sung Hoon Jung, Changwon-si (KR); Yu Ri Lee, Incheon (KR); Doo Ho Choi, Gimhae-si (KR); Byoung Joon Kim, Changwon-si (KR)

(73) Assignee: KOREA INSTITUTE OF MATERIALS SCIENCE, Changwon-si (KR)

( * ) Notice: Subject to any disclaimer, the term of this patent is extended or adjusted under 35 U.S.C. 154(b) by 74 days.

(21) Appl. No.: 16/097,638

(22) PCT Filed: Sep. 29, 2017

(86) PCT No.: PCT/KR2017/011061
§ 371 (c)(1),
(2) Date: Oct. 30, 2018

(87) PCT Pub. No.: WO2019/066113
PCT Pub. Date: Apr. 4, 2019

(65) Prior Publication Data
US 2021/0112651 A1  Apr. 15, 2021

(51) Int. Cl.
*H05H 1/24* (2006.01)
*A61N 1/04* (2006.01)
(Continued)

(52) U.S. Cl.
CPC .......... *H05H 1/2406* (2013.01); *A61L 2/0011* (2013.01); *A61L 2/14* (2013.01);
(Continued)

(58) Field of Classification Search
CPC . A61L 2/0011; A61L 2/14; A61L 2/26; A61L 9/22; A61N 1/0412; A61N 1/327;
(Continued)

(56) References Cited

U.S. PATENT DOCUMENTS

| | | | |
|---|---|---|---|
| 9,226,790 B2 * | 1/2016 | Zemel | A61B 18/042 |
| 10,265,116 B2 * | 4/2019 | Stieber | A61N 1/44 |

(Continued)

FOREIGN PATENT DOCUMENTS

| | | |
|---|---|---|
| JP | 2014-505553 | 3/2014 |
| KR | 100696532 B1 * | 3/2007 |

(Continued)

OTHER PUBLICATIONS

KR10-1012442B—English translation (Year: 2011).*
(Continued)

*Primary Examiner* — Alexander W Keeling
(74) *Attorney, Agent, or Firm* — Lex IP Meister, PLLC

(57) ABSTRACT

The disclosure relates to a flexible active species generator comprising: a first electrode of a conductive metal thin film; a second electrode of a ground electrode; a flexible dielectric layer of an insulator formed between the first electrode and the second electrode; and a plasma resistant functional layer formed between the dielectric layer and the second electrode, wherein the first electrode and the second electrode are electrically connected to an external power supply to generate an atmospheric pressure plasma to generate active species. The flexible active species generator has a plasma resistant function to prevent deformation and decomposition of an insulator caused by the plasma as well as an active species generating function from atmospheric pressure plasma, and has durability and safety, which is thus applicable to articles, foods, garments and human body in various forms.

13 Claims, 13 Drawing Sheets

(51) Int. Cl.
*A61N 1/32* (2006.01)
*A61L 2/00* (2006.01)
*A61L 2/14* (2006.01)
*A61L 2/26* (2006.01)
*A61L 9/22* (2006.01)
*C02F 1/30* (2006.01)
*C02F 1/46* (2006.01)
*A23L 3/26* (2006.01)

(52) U.S. Cl.
CPC .............. *A61L 2/26* (2013.01); *A61L 9/22* (2013.01); *A61N 1/0412* (2013.01); *A61N 1/327* (2013.01); *C02F 1/30* (2013.01); *C02F 1/4608* (2013.01); *A23L 3/263* (2013.01); *A23V 2002/00* (2013.01); *A61L 2202/11* (2013.01); *A61L 2202/21* (2013.01); *C02F 2201/483* (2013.01); *C02F 2303/04* (2013.01)

(58) Field of Classification Search
CPC .............. C02F 1/30; C02F 1/4608; H05H 1/2406–1/2465
See application file for complete search history.

(56) References Cited

U.S. PATENT DOCUMENTS

| | | | | |
|---|---|---|---|---|
| 2005/0045107 | A1* | 3/2005 | Koroyasu | H01J 37/32559 118/728 |
| 2010/0119843 | A1* | 5/2010 | Sun | H01J 37/32477 428/426 |
| 2011/0272098 | A1* | 11/2011 | Nonomura | H01J 37/32935 156/345.26 |
| 2012/0259270 | A1* | 10/2012 | Wandke | A61N 1/0476 604/23 |
| 2012/0296265 | A1* | 11/2012 | Dobrynin | A61N 1/44 604/23 |
| 2015/0137677 | A1* | 5/2015 | Sohn | A61L 9/22 313/268 |
| 2015/0151135 | A1* | 6/2015 | Kalghatgi | A61P 37/04 604/20 |
| 2015/0209595 | A1* | 7/2015 | Kalghatgi | A61N 1/44 604/20 |
| 2019/0184187 | A1* | 6/2019 | Lee | A61N 1/0408 |

FOREIGN PATENT DOCUMENTS

| | | | | |
|---|---|---|---|---|
| KR | 10-2008-0005968 | | 1/2008 | |
| KR | 10-2010-0102883 | | 9/2010 | |
| KR | 10-1012442 B | * | 2/2011 | |
| KR | 10-2012-0103415 | | 9/2012 | |
| KR | 10-2013-0108015 | | 10/2013 | |
| KR | 10-2013-0114525 | | 10/2013 | |
| KR | 10-1391708 | | 5/2014 | |
| KR | 1020150030225 | * | 3/2015 | |
| KR | 10-2015-0111064 | | 10/2015 | |
| KR | 10-2016-0021477 | | 2/2016 | |
| KR | 10-2017-0066314 | | 6/2017 | |
| WO | WO-2005044366 A2 | * | 5/2005 | ........ A61M 37/0015 |
| WO | 2013/105659 | | 7/2013 | |
| WO | 2013-105659 | | 7/2013 | |

OTHER PUBLICATIONS

KR1020150030225 _ English translation (Year: 2015).*
KR-100696532-B1—English translation (Year: 2007).*
KIPO, Office Action of KR 10-2017-0126785 dated Oct. 21, 2019.
KIPO, Office Action of Application No. 10-2015-0022675, dated Jul. 7, 2021.
KIPO, Office Action of KR 10-2017-0126785 dated on Dec. 17, 2018.

* cited by examiner

FLEXIBLE ACTIVE SPECIES GENERATOR AND USE THEREOF

CROSS-REFERENCE TO RELATED APPLICATION(S)

This application claims the benefit under 35 USC 119(a) of PCT/KR2017/011061 filed on Sep. 29, 2017, the entire disclosure of which is incorporated herein by reference for all purposes.

BACKGROUND

1. Field

This disclosure relates to a flexible active species generator and its use. More particularly, this disclosure relates to an active species generator having a plasma resistant function of preventing deformation and decomposition of an insulator to improve durability and safety in addition to an active species generating function from atmospheric pressure plasma.

2. Description of Related Art

In recent years, demand for flexible materials is continuously increasing in order to be applied to flexible electronic devices such as flexible displays and wearable devices in various fields such as computers, mobile phones, and medical devices. In the fields of medical, clothing and food, there is a rapid increase in demand for materials and devices having antibacterial or sterilizing functions applicable to flexible medical tools, medical tool packing articles, sports clothing, food packing articles, and the like.

Generally, sterilization methods for various pathogens are classified into a thermal sterilization and a non-thermal sterilization. The thermal sterilization is a sterilization method in which a material is heated at a temperature of about 60° C. or more for 30 minutes or more. However, a flexible material composed mostly of a polymer is not applicable because it shows degeneration and distortion in a high temperature environment. In addition, the thermal sterilization is disadvantageous in that it cannot be applied to human body, garment, fresh food, and the like.

The non-thermal sterilization includes ultra-high pressure, ohmic heating, radiation ray (gamma ray) irradiation, ultraviolet (UV) irradiation and the like. The non-thermal sterilization has advantages of reducing energy use, reducing discharge of pollutants, and greatly improving productivity. On the other hand, it cannot be popularized due to disadvantages of poor sterilization reliability compared to the thermal sterilization, requiring facilities for installation, maintenance and management for its specific method and facility, and being difficult to be popularized.

A technique for compensating for such disadvantages of the non-thermal sterilization is to generate active species using atmospheric pressure low-temperature plasma of this disclosure. A typical technology of generating active species using electrical energy has been applied not only to sterilization but also to water treatment, surface treatment of fibers and packaging materials, smoke decomposition, semiconductor cleaning and the like. The above-described technology can be used semi-permanently and applicable to various fields because the cost of facilities and equipment is lower than that of other non-thermal sterilizations. In addition, it can be easily applied in life environments because of low human damage which can be caused by high magnetic field and radiation.

KR Patent Publication No. 10-2010-0102883 (Sep. 27, 2010) describes an example of a method for sterilizing an object contaminated with microorganism using atmospheric pressure plasma.

Korean Patent Registration No. 1391708 (Apr. 28, 2014) describes an example of a method for sterilizing packaged food using atmospheric plasm and packaged food manufactured thereby.

In addition, KR Patent Publication No. 10-2016-0021477 (Feb. 26, 2016) describes an example of a plasma sterilization film and a plasma sterilization packaging apparatus.

Since an active species generator includes an electrode, an insulator must be included. The insulator of the flexible active species generator is a polymer material, which is easily decomposed by active species and thus has a low insulation performance, which makes it difficult to use continuously, and also generates harmful components due to decomposition.

It is generally known that cosmetics and the like, which are transmitted through the skin, cannot transmit the epidermis of about 0.2 mm thickness and an amount of an effective material transmitted and absorbed to the dermis is thus very small. There are few studies to dramatically increase delivery of effective materials such as cosmetics through the skin.

SUMMARY

An object of this disclosure is to provide a flexible active species generator having plasma resistant function of preventing deformation and decomposition of an insulator caused by plasmas well as an active species generating function from atmospheric pressure plasma, which is able to improve durability and safety.

Another object of this disclosure is to provide a flexible active species generator having an electric shock prevention function, a discharge voltage reduction function, a self-cleaning function, a super water-repellent function or a light-emitting function.

Still another object of this disclosure is to provide an article having sterilization, air purification, water repellency, light-emitting, deodorization, skin improvement or water treatment functions in which the flexible active species generator is attached to or integrated with a human body or an object.

Still another object of this disclosure is to provide a flexible active species generator capable of efficiently delivering effective materials of cosmetics and drugs through the skin.

According to one aspect of this disclosure, there is provided a flexible active species generator comprising: a first electrode of a conductive metal thin film; a second electrode of a ground electrode; a flexible dielectric layer of an insulator formed between the first electrode and the second electrode; and a plasma resistant functional layer formed between the dielectric layer and the second electrode, wherein the first electrode and the second electrode are electrically connected to an external power supply to generate an atmospheric pressure plasma to generate active species.

According to an embodiment of this disclosure, the functional layer may prevent physical or chemical changes in the dielectric layer.

According to an embodiment of this disclosure, the functional layer may be selected from $Al_xO_y$, $SiO_x$, $SiO_xC_yH_z$, a-C, and a-C:H.

According to an embodiment of this disclosure, the second electrode may be in a lattice or porous form.

According to an embodiment of this disclosure, the dielectric layer may be selected from polymer, flexible glass, fabric, and paper.

According to an embodiment of this disclosure, the dielectric layer may have super water repellency.

According to an embodiment of this disclosure, the functional layer may reduce discharge voltage by coating with an oxide that generates secondary electrons.

According to an embodiment of this disclosure, the oxide may be one selected from strontium oxide (SrO), calcium oxide (CaO), alkali antimonide, beryllium oxide (BeO), magnesium oxide (MgO), gallium phosphide (GaP), gallium arsenide phosphide (GaAsP), and lead oxide (PbO).

According to an embodiment of this disclosure, the functional layer may further include a self-cleaning layer, a super water-repellent layer, a light-emitting layer, or a mixed layer thereof.

According to an embodiment of this disclosure, the functional layer may be formed in a plurality of layers, and may further include a self-cleaning layer, a super water-repellent layer, a light-emitting layer, or a mixed layer thereof between the plasma resistant functional layer and the second electrode.

According to an embodiment of this disclosure, the self-cleaning layer may be selected from anatase $TiO_2$, rutile $TiO_2$, ZnO, CdS, $ZrO_2$, $SnO_2$, $V_2O_2$, $WO_3$ and $SrTiO_3$.

According to an embodiment of this disclosure, the super water-repellent layer may be formed by forming or controlling a nanostructure on the surface of the functional layer.

According to an embodiment of this disclosure, at least one of the first electrode and the second electrode may be formed of a flexible conductive material.

According to an embodiment of this disclosure, at least one of the first electrode and the second electrode may be formed of a transparent conductive material.

According to an embodiment of this disclosure, the second electrode may be formed of a porous conductive material, a fabric conductive material, or a combination thereof.

According to an embodiment of this disclosure, at least one of the first electrode and the second electrode may be selected from Ag nanoparticle (AgNP), Ag nanowire (AgNW) and metal embedded transparent conductive electrode (ME-TCE).

According to an embodiment of this disclosure, the dielectric layer may be formed of one selected from polyethylene terephthalate (PET), polyimide (PI), polycarbonate (PC), polyethylene (PE), polyurethane (PU), poly-methyl methacrylate (PMMA), polystyrene (PS), polytetrafluoroethylene (PTFE), polydimethylsiloxane (PDMS), and a mixture thereof.

According to an embodiment of this disclosure, the dielectric layer may include a first dielectric layer formed on the bottom part and the side parts of the first electrode, and a second dielectric layer formed on the upper part of the first electrode.

According to another aspect of this disclosure, there is provided an article having sterilization, air purification, deodorization, water repellency, light-emitting, skin improvement, hemostasis, or water treatment functions in which the flexible active species generator is attached to or integrated with a human body or an object.

According to an embodiment of this disclosure, the article may be a container, an interior article, a clothes, a mask, a patch for attaching to a human body, a hemostatic band, or a water treatment device.

According to an embodiment of this disclosure, the container may be a food storage container or a blood storage container.

According to an embodiment of this disclosure, the article may include a power transceiver in which the first electrode to which a high voltage is applied is not exposed.

According to an embodiment of this disclosure, the second electrode may be in a porous form and the article may be a hemostatic band.

According to another aspect of this disclosure, there is provided a flexible active species generator comprising: a first electrode of a conductive metal thin film; a second electrode of a ground electrode; a flexible dielectric layer of an insulator formed between the first electrode and the second electrode; and a plasma resistant functional layer formed between the dielectric layer and the second electrode, wherein the first electrode and the second electrode are electrically connected to an external power supply to generate an atmospheric plasma to generate active species, and at least one of the second electrode, the dielectric layer, and the plasma resistant functional layer includes an effective material.

According to an embodiment of this disclosure, at least one selected from the second electrode and the plasma resistant functional layer including an effective material may be formed of a flexible conductive material.

According to an embodiment of this disclosure, the dielectric layer including an effective material may be formed of a flexible non-conductive material.

According to an embodiment of this disclosure, the effective material may have at least one activity selected from cosmetic activity, antibacterial activity, anticancer activity, and antiviral activity.

According to an embodiment of this disclosure, the effective material may be at least one selected from a plant extract, a physiologically active material, an anticancer agent, and a vaccine.

According to an embodiment of this disclosure, the plant extract may be at least one water or alcohol extract selected from tangerine peel, *Camelia sinensis, Cnidii fructus, Schisandrae fructus, Poria cocos, Lycii fructus, Morus alba Linne, Polygonatum odoratum* var. *Pluriflorum, Psoralea corylifolia*, fruit of *Ligustrum japonicum Thunb, Olibanum*, peel of *Cudrania tricuspidata* (Carr.) *Bureau, Diospyros kaki* leaf, propolis, *Calendula arvensis, Buplerum falcatum*, honey, *Sophora flavescens*, and *Centella asiatica*.

According to an embodiment of this disclosure, the physiologically active material may be at least on selected from caffeic acid, anomalin, adonitol, flavonoid, saponin, rutin, glutamic acid, quercetin, and astaxanthin.

According to an embodiment of this disclosure, the anticancer agent may be at least one selected from dacarbazine, cisplatin, vinblastine, taxol, and anti-programmed death-1 enzyme.

According to an embodiment of this disclosure, the vaccine may be at least one killed vaccine selected from influenza, cholera, and measles vaccine.

According to an embodiment of this disclosure, the functional layer may include an additional functional layer.

According to an embodiment of this disclosure, the effective material may be included in the functional layer in contact with the second electrode or may be coated on the functional layer.

According to an embodiment of this disclosure, the flexible active species generator may further include a plurality of fine pore-forming structures formed on the functional layer in contact with the second electrode to form fine pores in the epidermis of an organism.

According to an embodiment of this disclosure, the effective material may be included in the second electrode or coated on the second electrode.

According to an embodiment of this disclosure, the flexible active species generator may further include a plurality of fine pore-forming structures formed on the second electrode to form fine pore in the epidermis of an organism.

According to an embodiment of this disclosure, the fine pore-forming structure may include an effective material which is the same as or different from the effective material included in or coated on the functional layer or the second electrode.

According to an embodiment of this disclosure, the surface of the fine pore-forming structure may have a coating layer of an effective material which is the same as or different from the effective material included in or coated on the functional layer.

According to an embodiment of this disclosure, the front end part of the fine pore-forming structure may be sharp.

According to an embodiment of this disclosure, the longitudinal section of the fine pore-forming structure may be triangular.

According to an embodiment of this disclosure, the height of the fine pore-forming structure may be 50-300 μm, and the width of the fine pore-forming structure may be 10-300 μm.

According to an embodiment of this disclosure, the second electrode may be an organism.

According to another aspect of this disclosure, there is provided a flexible active species generator comprising: a first electrode of a conductive metal thin film; a second electrode of a ground electrode; and a flexible dielectric layer formed between the first electrode and the second electrode, wherein the first electrode and the second electrode are electrically connected to an external power supply to generate an atmospheric plasma to generate active species, and at least one of the second electrode and the dielectric layer comprises an effective material.

According to an embodiment of this disclosure, the flexible active species generator has a plasma resistant function to prevent deformation and decomposition of the insulator caused by the plasma in addition to an active species generating function from atmospheric pressure plasma and has durability and safety.

According to an embodiment of this disclosure, the flexible active species generator may provide an electric shock prevention function, a discharge voltage reduction function, a self-cleaning function, a super water-repellent function or a light-emitting function.

According to an embodiment of this disclosure, the flexible active species generator may be safely applicable to a food or blood storage container, a functional interior article, a functional clothes, a mask, a patch for attaching to a human body, a hemostatic band and a water treatment device, and have sterilization, air purification, self-cleaning, water repellency, light-emitting, prevention of skin aging, hemostasis, or water treatment functions.

According to an embodiment of this disclosure, the flexible active species generator may effectively deliver a plant extract, a physiologically active material, an anticancer agent, or a vaccine having cosmetic activity, antibacterial activity, anticancer activity, and antiviral activity through the skin.

Other through the skin objects and features will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

While the present disclosure has been described with reference to particular embodiments, it is to be appreciated that various changes and modifications may be made by those skilled in the art without departing from the spirit and scope of the present disclosure, as defined by the appended claims and their equivalents. Throughout the description of the present disclosure, when describing a certain technology is determined to evade the point of the present disclosure, the pertinent detailed description will be omitted.

While such terms as "first" and "second," etc., may be used to describe various components, such components must not be limited to the above terms. The above terms are used only to distinguish one component from another.

The terms used in the description are intended to describe certain embodiments only, and shall by no means restrict the present disclosure. Unless clearly used otherwise, expressions in the singular number include a plural meaning. In the present description, an expression such as "comprising" or "consisting of" is intended to designate a characteristic, a number, a step, an operation, an element, a part or combinations thereof, and shall not be construed to preclude any presence or possibility of one or more other characteristics, numbers, steps, operations, elements, parts or combinations thereof.

The flexible active species generator according to certain embodiments of the disclosure will be described below in more detail with reference to the accompanying drawings, in which those components are rendered the same reference number that are the same or are in correspondence, regardless of the figure number, and redundant explanations are omitted.

Figure 1:
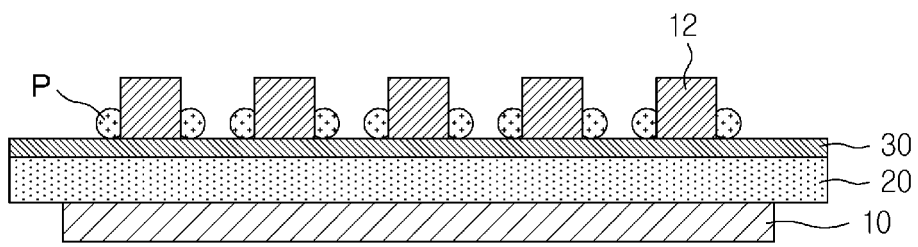
FIG. 1 is a cross-sectional view illustrating a flexible active species generator according to an embodiment of this disclosure.
Figure 2:
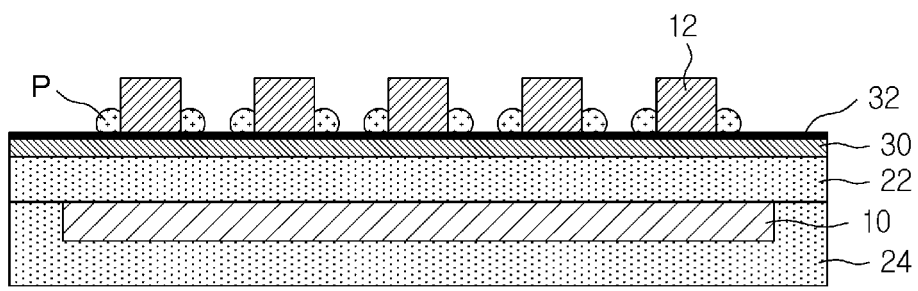
FIG. 2 is a cross-sectional view illustrating a flexible active species generator according to another embodiment of this disclosure.

FIG. 1 is a cross-sectional view illustrating a flexible active species generator according to an embodiment of this disclosure. FIG. 2 is a cross-sectional view illustrating a flexible active species generator according to another embodiment of this disclosure According to one aspect of this disclosure, a flexible active species generator 100 of this disclosure comprises a first electrode 10 of a conductive metal film; a second electrode 12 of a ground electrode; a flexible dielectric layer 20 of an insulator formed between the first electrode 10 and the second electrode 12; and a plasma resistant first functional layer 30 formed between the dielectric layer 20 and the second electrode 12, wherein the first electrode 10 and the second electrode are electrically connected to generate atmospheric pressure plasma P to generate active species.

In this disclosure, active species generation is conducted by plasma generation. Electricity is mainly used to decompose atmospheric gas composed of nitrogen, oxygen, moisture and carbon dioxide at about 1 atmospheric pressure. Plasma generation is a typical method for generating active species using electric energy. An electric field of about 30 kV/cm or more is required to generate plasm at 1 atmospheric pressure and discharge occurs when the electric field is applied to the gap between metals. At this time, an insulator or a dielectric is inserted in order to maintain a stable discharge and to suppress increase of an excessive discharge voltage. There is an atmospheric pressure dielectric barrier discharge (DBD) as a representative method.

The atmospheric pressure dielectric barrier discharge is generated by the application of an alternating voltage of a few kHz to several tens of MHz to one or more electrodes, wherein a dielectric barrier is placed in the gap between two separated electrodes to prevent the flow of direct current. The dielectric barrier prevents over-flow of the DC current, and thus prevents the transition of the discharge into an arc, so that a low-temperature plasma with a gas temperature of several tens of degrees centigrade at 1 atmospheric pressure can be maintained.

In this disclosure, the "active species" includes reactive species generated from the low-temperature plasma, such as reactive oxygen species (ROS) including oxygen ions (O, $O^{2+}$), ozone ($O_3$), reactive nitrogen species (RNS), hydroxyl group (OH), and the like. However, it is not limited thereto. In this disclosure, active species have the function of disinfection or sterilization, which destroys the cell walls of pathogens and microorganisms and reduces vital functions.

According to an embodiment of this disclosure, the first electrode 10 is a voltage application electrode for generating dielectric barrier plasma. The first electrode 10 may be embedded in the dielectric layer 20 or attached to the lower part of the dielectric layer 20. However, it is appreciated that the first electrode 10 be embedded in the dielectric layer 20 to prevent electric shock when used for attachment to the human body. As shown in FIG. 1 and FIG. 2, the first electrode 10 may be formed of a flat plane of a conductive metal thin film or formed in a patterned form. However, it is not limited thereto.

According to an embodiment of this disclosure, the second electrode 12 is a ground electrode with no voltage applied. It may be provided to be contacted with human body and an object to be treated. Thus, various configurations of electrodes may be possible.

According to an embodiment of this disclosure, the second electrode 12 may be formed in a porous or patterned shape arranged at regular intervals. However, it is not limited thereto. The patterned shape may be a line or lattice (mesh) shape, preferably a lattice shape, formed of a plurality of lines to expose a part of the dielectric layer. When a voltage is applied to the first electrode 10, an atmospheric pressure plasma P is generated between the second electrodes 12. As shown FIG. 1 and FIG. 2, the second electrode 12 may be pattern-exposed on the first electrode 10 with the dielectric layer 20 interposed therebetween. The second electrode 12 may be formed on the same plane as the first electrode 10 or may be formed in a pattern depression shape (not shown).

According to an embodiment of this disclosure, at least one of the first electrode 10 and the second electrode 12 may be formed of a flexible conductive material.

According to an embodiment of this disclosure, the second electrode 12 may be formed of a porous conductive material, a fabric conductive material, or a combination thereof.

According to an embodiment of this disclosure, at least one of the first electrode 10 and the second electrode 12 may be formed of a transparent conductive material.

According to an embodiment of this disclosure, the first electrode 10 and the second electrode 12 may be formed of at least one selected from Fe, Cr, Ni, Al, Cu, Ag and carbon composites including carbon nanotubes, carbon nanofibers, and the like.

According to an embodiment of this disclosure, the first electrode 10 and the second electrode 12 may be made of a material that is flexible, highly transparent, high conductive, and easy to pattern. The first electrode 10 and the second electrode 12 may be formed of one selected from Ag nanoparticle (AgNP), Ag nanowire (AgNW) and metal embedded transparent conductive electrode (ME-TCE). However, it is not limited thereto.

According to an embodiment of this disclosure, the first electrode 10 and the second electrode 12 may be formed by a variety of methods including electroplating, gravure, inkjet printing, slot die coating, sputtering, vacuum evaporation, arc deposition, plasma deposition, annealing, adhesive adhesion, and EHD. The first electrode 10 and the second electrode 12 may be also formed by mask deposition and lithography for high speed production of a large area. However, it is not limited thereto.

According to an embodiment of this disclosure, the dielectric layer 20 is positioned between the first electrode 10 and the second electrode 12 so that the discharge generated in the gap between the electrodes to which voltage is applied prevents the transition to high current discharge and also prevents electric shock accident when attached to a human body.

According to an embodiment of this disclosure, the dielectric layer 20 may be formed of one selected from polymer, flexible glass, fabric, and paper that can maintain flexibility with the electrodes that produce the active species. The dielectric layer 20 may be formed of a material having low dielectric breakdown associated with heat generated by electric energy applied to generate the active species and a voltage applied to the electrode.

According to an embodiment of this disclosure, the dielectric layer 20 may be made of a transparent material. When the dielectric layer 20 is transparent and the active species generator is attached or integrated to a product, it can be used in a variety of products, without causing any problem in the appearance of the product.

According to an embodiment of this disclosure, as shown in FIG. 2, the dielectric layer 20 may be formed of a first dielectric layer 24 disposed on the bottom part and the side parts of the first electrode 10; and a second dielectric layer 22 formed on top part of the first electrode 10. The first dielectric layer 24 may be formed of a material having high dielectric breakdown voltage, transparency and high flexibility. The second dielectric layer 22 may be also formed of a material having high dielectric breakdown voltage, heat resistance and high flexibility.

According to an embodiment of this disclosure, the dielectric layer 20 is formed of a material selected from polyethylene terephthalate, polyimide, polycarbonate, polyethylene, polyurethane, poly-methyl methacrylate, polystyrene, polytetrafluoroethylene, polydimethylsiloxane, and a mixture thereof. However, it is not limited thereto.

According to an embodiment of this disclosure, the dielectric layer 20 may be configured to have super-water repellent or super-blood repellent properties by using Teflon, which is a super water repellent dielectric material, without a separate super water-repellent layer.

According to an embodiment of this disclosure, the dielectric layer 20 may be formed by a variety of known methods such as adhesion, solution curing, and the like.

Figure 3:
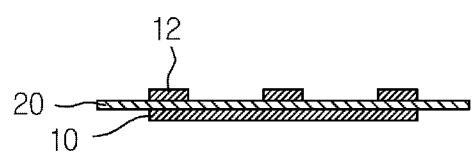
FIG. 3 is a cross-sectional view and a plasma discharge image (right) illustrating a flexible active species generator with a plasma resistant functional layer according to an embodiment of this disclosure, and a cross-sectional view and a plasma discharge image (left) illustrating a flexible active species generator without a plasma resistant functional layer.
Figure 3:
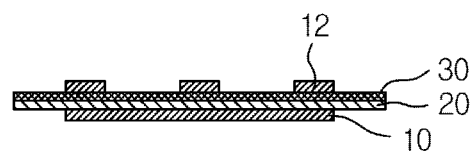
Figure 3:
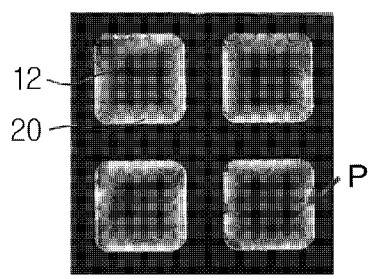
Figure 3:
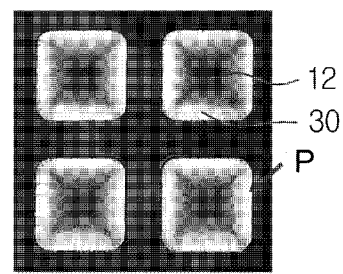

According to an embodiment of this disclosure, the first functional layer 30 is formed between the dielectric layer 20 and the second electrode 12 to prevent physical or chemical changes in the dielectric layer 20 as a plasma resistant. The first functional layer 30 prevents deformation and decomposition of the dielectric layer 20 and improves the durability of the active species generator to enable continuous use. A typical active species generator lowers transparency and tears a hole in sever case because the dielectric layer 20 changes to white due to plasma when it is used a long period of time. However, this problem can be solved by this disclosure. Also, generation of harmful materials due to deformation and decomposition of the dielectric layer 20 composed of a polymer or the like can be prevented, and the active species generator can be thus safely used (see FIG. 3 to FIG. 5).

According to an embodiment of this disclosure, the material of the first functional layer 30 is not particularly limited as long as it has plasma resistant and high dielectric breakdown voltage properties. The first functional layer 30 is formed of one selected from $Al_2O_3$, $SiO_x$, $SiO_xC_yH_z$, a-C and a-C:H, preferably $SiO_2$. However, it is not limited thereto.

According to an embodiment of this disclosure, the first functional layer 30 may be formed by sputtering, PECVD, or $Ar/H_2$ ion beam. However, it is not limited thereto and may be formed by various known methods.

According to an embodiment of this disclosure, the first functional layer 30 may include at least one of a self-cleaning layer, a super water-repellent layer, a light-emitting layer, or a mixed layer thereof.

According to an embodiment of this disclosure, the first functional layer 30 may be formed in a single layer or a plurality of layers and may further include a second functional layer (32 in FIG. 6) selected from a self-cleaning layer, a super water-repellent layer, a light-emitting layer, or a mixed layer thereof between the plasma resistant first functional layer 30 and the second electrode 12.

According to an embodiment of this disclosure, the self-cleaning layer may be selected from anatase $TiO_2$, rutile $TiO_2$, ZnO, CdS, ZrO2, $SnO_2$, $V_2O_2$, $WO_3$ and $SrTiO_3$, preferably $TiO_2$. However, it is not limited thereto. $TiO_2$ is a catalyst that has self-cleaning or purifying functions such as decomposing pollutants by light as a photocatalyst. $TiO_2$ can be excited by UV generated by active species transition on the dielectric layer to effectively decompose pollutants.

According to an embodiment of this disclosure, the super water-repellent layer may be configured to have super water repellent properties by forming or controlling nanostructures on the surface of the functional layer. The super water-repellent layer may provide the effect of the medical patch even in the case of blood leakage when the active species generator is used as a medical patch.

As described above, the dielectric layer may be configured to have super water-repellent or super super-blood properties without using the super water-repellent layer by using Teflon, which is a super water-repellent dielectric material.

In an embodiment of this disclosure, the light-emitting layer that emits light by UV light or the like generated by active species on the flexible material layer may be additionally formed as a functional layer to simultaneously have a light emitting effect.

Figure 6:
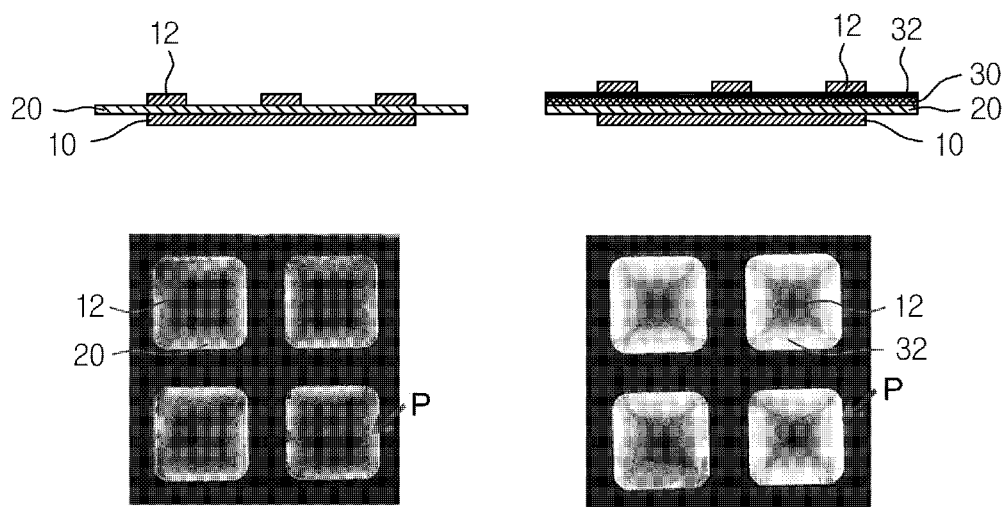
FIG. 6 is a cross-sectional view and a plasma discharge image (right) illustrating a flexible active species generator coated with a secondary electron-generating oxide on a functional layer according to an embodiment of this disclosure, and a cross-sectional view and a plasma discharge image (left) illustrating a flexible active species generator not coated with a secondary electron-generating oxide on a functional layer.

As shown in FIG. 6, according to an embodiment of this disclosure, the first functional layer 30 may include an additional second functional layer 32 coated with an oxide that generates secondary electrons to reduce discharge voltage. The oxide may have a high secondary electron generation coefficient, generate more electrons at the same discharge voltage by the compound, and stably maintain a low voltage. Thereby, the probability of dielectric breakdown can be reduced, and stable operation can be achieved by keeping stably the low voltage. Also, this disclosure can lead to an increase in electrical efficiency and an improvement in the lifetime of the active species generator since lowering the discharge voltage can reduce heat generation and electrical stress to the system.

According to an embodiment of this disclosure, the oxide may be selected from strontium oxide (SrO), calcium oxide (CaO), alkali antimonide, beryllium oxide (BeO), magnesium oxide (MgO), gallium phosphide (GaP), gallium arsenide phosphide (GaAsP), and lead oxide (PbO). However, it is not limited thereto.

According to an embodiment of this disclosure, the discharge voltage may be at a level of 1 kV to 2 kV, which is low enough to be applicable for portable or human body attachment. However, it is not limited thereto.

According to an embodiment of this disclosure, the discharge power per unit area of the flexible active species generator including the functional layer coated with the compound on the top part may be from $0.13 \text{ W/mm}^2$ to $0.2 \text{ W/mm}^2$. When the discharge power per unit area is larger, it is possible to generate more active species per unit area (see FIG. 4 to FIG. 8). Thus, the results indicate that the operational stability of the flexible active species generator is improved by the first functional layer 30 coated with the compound on the top part.

Figure 9:
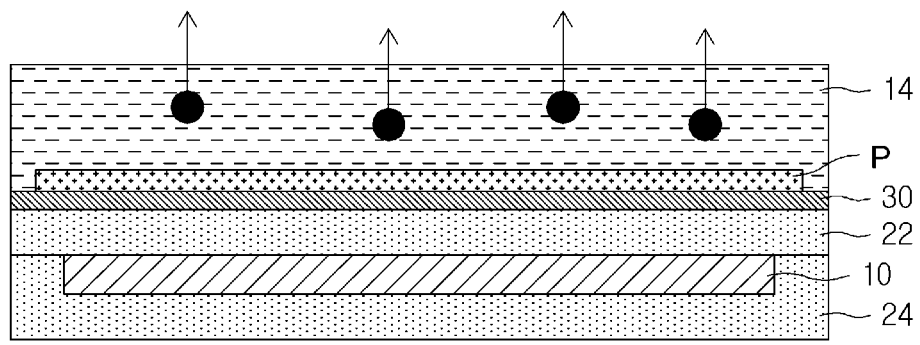
FIG. 9 is a cross-sectional view illustrating a flexible active species generator having a porous second electrode according to an embodiment of this disclosure.

FIG. 9 is a cross-sectional view illustrating a flexible active species generator having a porous second electrode according to an embodiment of this disclosure.

According to an embodiment of this disclosure, the second electrode 14 is made of a porous material, and the flexible active species generator 200 can be thus used as a hemostatic band for blood coagulation. A thickness of the second electrode 14 made of the porous material may be 1-10 mm, but is not limited thereto. The porous material may be any of various known porous materials, for example, porous Ni.

Figure 10:
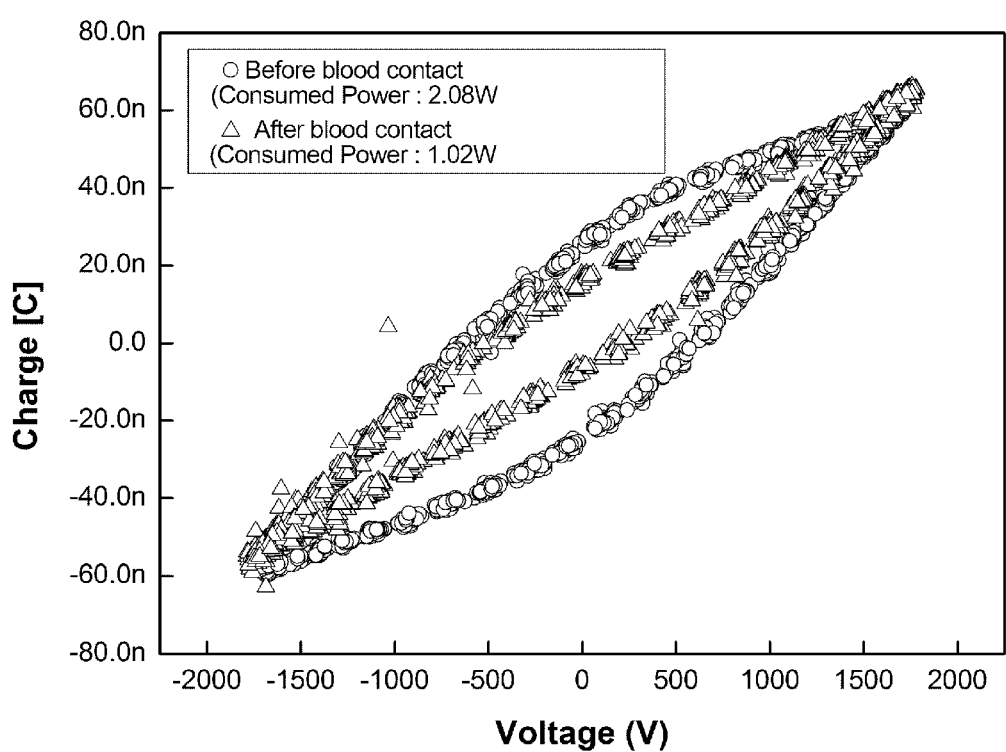
FIG. 10 is a Q-V lissajous diagram illustrating discharge power consumption before and after blood contact of a flexible active species generator having a lattice-shaped second electrode according to an embodiment of this disclosure.
Figure 11:
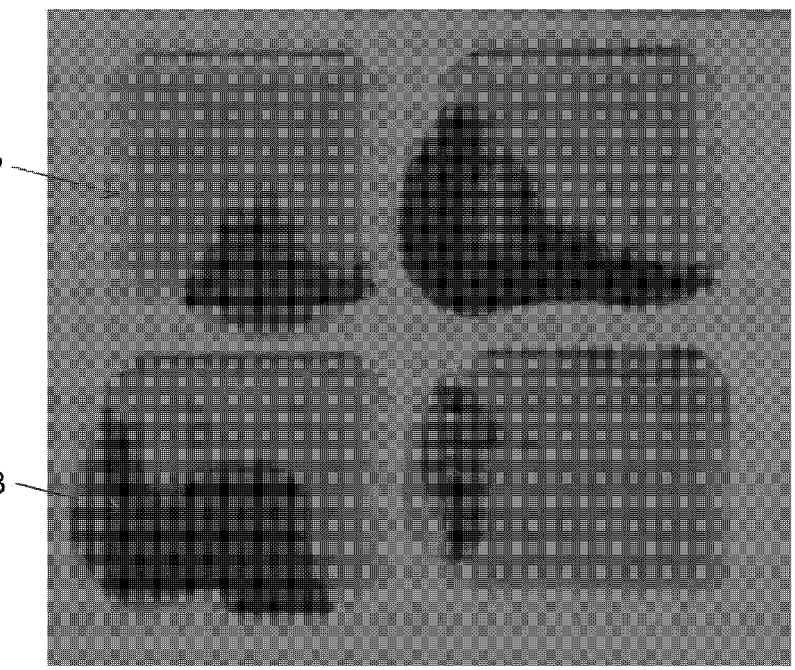
FIG. 11 is an image illustrating that discharge is not caused since the gap for generating active species is filled with blood after blood contact of a flexible active species generator having a lattice-shaped second electrode according to an embodiment of this disclosure.

When the second electrode is formed in a mesh shape of 1 mm or less, the gap between the second electrode and the dielectric layer where the discharge is generated is filled with blood to prevent the generation of active species R (see FIG. 9 to FIG. 11). Accordingly, the second electrode 14 made of porous material can provide the effect of the hemostasis band using an active species generator, so that blood generated on the surface of a human body is not filled in the gap between the second electrode 14 and the dielectric layer 22 to maintain the gap in an empty state.

According to another aspect of this disclosure, there is provided an article having sterilization, air purification, water repellency, light-emitting, skin improvement, hemostasis or water treatment functions in which the flexible active species generator of this disclosure is attached to or integrated with a human body or an object. According to this disclosure, the article provides plasma resistance, ultraviolet and electron-induced antimicrobial, sterilization, self-cleaning, super-water repellency, light-emitting, skin improvement, hemostasis or water treatment functions by the functional layer or the dielectric layer.

According to an embodiment of this disclosure, the article may be a container, an interior article, a garment, a mask, a patch for attaching to a human body, a hemostatic band or a water treatment device.

According to an embodiment of this disclosure, the container may be a food storage container or a blood storage container. However, it is not limited thereto. The container can sterilize the microorganisms by the active species that are generated and prolong a preservation period of the contents such as food. The container can effectively decompose odorous materials such as sulfur compounds, carbonyl compounds, and $NH_3$ through gas discharge. The container may be composed of one selected from glass, PET, HDPE, LDPE, PP, PI, PE, PS, PTFE, PDMS, and PC. However, it is not limited thereto.

According to an embodiment of this disclosure, the container may include a power transceiver in which the first electrode to which high voltage is applied is not exposed.

According to an embodiment of this disclosure, the container may include a wireless power transceiver. In the case where the wireless power transceiver is provided, for example, a system capable of sterilizing food in a container for a necessary period of time can be implemented by applying a voltage wirelessly even in a refrigeration storage system.

According to an embodiment of this disclosure, a functional interior article is provided, wherein the flexible active species generator according to embodiments of this disclosure is attached or integrated to provide sterilization and air cleaning functions.

According to an embodiment of this disclosure, the flexible active species generator can be utilized as an air purifier applicable to functional interior articles. In addition to curtains and blinds used in flexible forms such as textiles in existing interior articles, the flexible active species generator can be attached or integrated into wallpapers. In particular, curtains, blinds, wallpapers, and the like have a very large surface area and can function as an air purifier for improving indoor air quality.

The flexible active species generator combined with fabric or paper material can be used as an antibacterial/sterilizing functional interior article and air purifier (cleaner). In addition, volatile organic compounds (VOC) and benzene, which are known to be the main causes of sick house syndrome and atopy, can be effectively decomposed and thus, the flexible active species generator can be effectively used for indoor air quality improvement.

According to an embodiment of this disclosure, there is provided a functional garment characterized in that the flexible active species generator according to embodiments of this disclosure is attached or integrated to provide an antibacterial or deodorant function. Recently, a variety of products including antimicrobial and deodorant functions among sportswear and functional garments are becoming more and more popular. The active species generator of this disclosure can remove odors by decomposing uric acids caused by sweat in the human body.

In addition, the flexible active species generator can reduce inflammation caused by pollutants accumulated between clothes and skin when the clothes cannot be washed for a long time. When the flexible active species generator including the first functional layer 30 such as $TiO_2$ having a self-cleaning function is attached to clothes, $TiO_2$ excited by UV generated from the active species may decompose more effectively pollutants on the skin surface.

According to an embodiment of this disclosure, a human body patch is provided wherein a flexible active species generator according to embodiments of this disclosure is attached or integrated. The flexible active species generators of this disclosure can be used to improve skin aging and wrinkles by stimulating endothelial cells of the skin by patching it directly to the skin rather than to clothing.

According to an embodiment of this disclosure, a water treatment apparatus is provided wherein a flexible active species generator according to embodiments of this disclosure is attached or integrated. The water treatment apparatus may be added to water to sterilize water, and an electrode embedded flexible material layer may be wound in a coil shape.

According to an embodiment of this disclosure, the water treatment apparatus may include a power transceiver in which a first electrode to which a high voltage is applied is not exposed, so that a system capable of sterilizing water can be implemented by applying a voltage to the first electrode even in a humid environment or underwater environment.

Figure 15A:
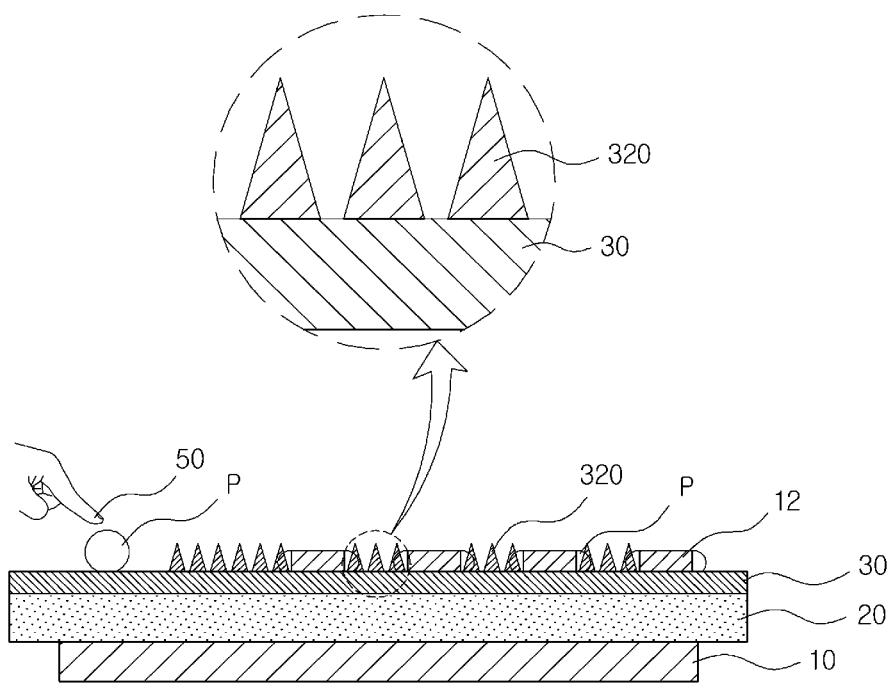
FIG. 15A is a schematic cross-sectional view illustrating a flexible active species generator according to an embodiment of this disclosure in which an effective material is included in a first functional layer and fine pore-forming structures are formed on the first functional layer.

FIG. 15A is a schematic cross-sectional view illustrating a flexible active species generator according to an embodiment of this disclosure in which an effective material is included in a first functional layer and fine pore-forming structures 320 are formed on the first functional layer.

According to another aspect of this disclosure, there is provided a flexible active species generator comprising a first electrode 10 of a conductive metal film; a second electrode 12 as a ground electrode; a flexible dielectric layer 20 of an insulator formed between the first electrode 10 and the second electrode 12; and a plasma resistant first functional layer 30 formed between the dielectric layer 20 and the second electrode 12, wherein the first electrode 10 and the second electrode 12 are electrically connected to an external power supply to generate an atmospheric pressure plasma to generate active species, and at least one of the second electrode 12, the dielectric layer 20, and the plasma resistant first functional layer 30 includes an effective material.

Since the flexible active species generator generates active species and at least one of the second electrode 12, the dielectric layer 20, and the plasma resistant first functional layer 30 includes an effective material, it is possible to efficiently deliver the effective material through the skin of an organism when the active species is generated. That is, reactive oxygen nitrogen species(RONS) can form a pore by lipid oxidation, thereby making it as a path to transfer an effective material. Thus, the effective material included in the first functional layer 30 and the like can be efficiently delivered to the dermis.

According to an embodiment of this disclosure, at least one of the second electrode 12 and the plasma resistant first functional layer 30 including the effective material may be formed of a flexible conductive material. The flexible conductive material may be a gel in which the effective material is mixed. However, it is not limited thereto. The gel may be a hydrogel or an ionic gel.

According to an embodiment of this disclosure, the dielectric layer 20, which includes the effective material, may be formed of a flexible non-conductive material. The non-conductive material may be a gel in which the effective material is mixed. However, it is not limited thereto. The gel may be a hydrogel or an ionic gel.

According to an embodiment of this disclosure, the effective material is not particularly limited as long as it is a material that has an effective function for delivery to an organism through the skin. The effective material may be a material having at least one activity selected from cosmetic activity, antibacterial activity, anticancer activity, and antiviral activity.

According to an embodiment of this disclosure, the effective material may be at least one selected from plant extract, physiologically active material, anticancer agent, and vaccine.

The plant extract may be at least one water or alcohol extract selected from tangerine peel, *Camelia sinensis, Cnidii fructus, Schisandrae fructus, Poria Cocos, Lycii fructus, Morus alba Linne, Polygonatum odoratum* var. *Pluriflorum, Psoralea corylifolia*, fruit of *Ligustrum japonicum Thunb, Olibanum*, peel of *Cudrania tricuspidata* (Carr.) *Bureau,*

*Diospyros kaki* leaf, propolis, *Calendula arvensis, Buplerum falcatum*, honey, *Sophora flavescens*, and *Centella asiatica*.

However, it is not limited thereto. The plant extract may be a hydrothermal extract or an ethanol extract. However, it is not limited thereto.

The physiologically active material may be at least one selected from caffeic acid, anomalin, adonitol, flavonoid, saponin, rutin, glutamic acid, quercetin, and astaxanthin. However, it is not limited thereto.

The anticancer agent may be at least one selected from dacarbazine, cisplatin, vinblastine, taxol, and anti-programmed death-1 enzyme. However, it is not limited thereto.

The vaccine may be at least one killed bacterial vaccine selected from influenza, cholera, and measles vaccine. However, it is not limited thereto. In the case of a live bacterial vaccine, it may be inactivated at the time of generation of active species, so that a killed vaccine may be suitable.

According to an embodiment of this disclosure, the effective material may be included in the functional layer in contact with the second electrode or may be coated on the functional layer. As shown in FIG. 15A, the effective material may be included in the first functional layer 30 in contact with the second electrode 12 or may be coated on the first functional layer 30. However, if a second functional layer 32 of the first functional layer 30 is additionally formed, the effective material may be included in the second functional layer 32 in contact with the second electrode 12 or may be coated on the second functional layer 32 (See FIG. 16A to FIG. 16C).

According to an embodiment of this disclosure, a plurality of fine pore-forming structures 320 may be further included on the first functional layer 30 in contact with the second electrode 12 to form fine pores in the epidermis of an organism.

The fine pore-forming structure 320 can form fine pores by physically punching the epidermis of an organism when a flexible active species generator according to this disclosure is contacted with the skin to effectively transfer the effective material to the dermis under the epidermis. In addition, it can allow synergy effect with pores formed by lipid oxidation by the reactive oxygen nitrogen species (RONS) to transfer the effective material more efficiently.

The fine pore-forming structure 320 may be formed on the entire surface of the first functional layer 30 or on the surface other than the second electrode 12. The fine pore-forming structure 320 may be formed with a suitable number and density depending on the kind and concentration of the effective material, and condition of an object requiring the activity of the effective material.

According to an embodiment of this disclosure, a coating layer 321 may be formed with the same or different effective material as that included in the first functional layer 30 or coated on the first functional layer 30, on the surface of the fine pore-forming structure 320.

According to an embodiment of this disclosure, the front end part of the fine pore-forming structure 320 may be sharp. The fine pore-forming structure 320 may be in the form of a microneedle. When a flexible active species generator according to this disclosure is in contact with the skin of an organism, it allows easily forming fine pores in the epidermis of the organism. However, the shape is not limited thereto.

According to an embodiment of this disclosure, the longitudinal section of the fine pore-forming structure 320 may be triangular. When a flexible active species generator according to this disclosure is in contact with the skin of an organism, it allows physically penetrating the epidermis of the organism easily to form fine pores to provide durability of the fine pore-forming structure 320. However, the shape is not limited thereto.

In this disclosure, there is no particular limitation for size as long as the size allows for the fine pore-forming structure 320 to physically penetrate the epidermis of an organism without causing excessive irritation or damage to the epidermis of the organism.

According to an embodiment of this disclosure, the height of the fine pore-forming structure 320 may be 50-300 μm, and the width of the fine pore-forming structure 320 may be 10-300 μm. Although it is not limited thereto, if the height of the fine pore-forming structure 320 is less than 50 μm or the width is less than 10 μm, it may not be easy to form fine pores in an organism skin. On the other hand, if the height of the fine pore-forming structure 320 is more than 300 μm or the width is more than 300 μm, it may cause irritation or damage to the epidermis of the organism.

According to an embodiment of this disclosure, the second electrode 12 may be an organism. There is no particular limitation for the organism as long as it is a subject that requires at least one activity selected from cosmetic activity, antibacterial activity, anticancer activity, and antiviral activity. The organism may be mammalian, preferably human body 50. However, the shape is not limited thereto.

Figure 15B:
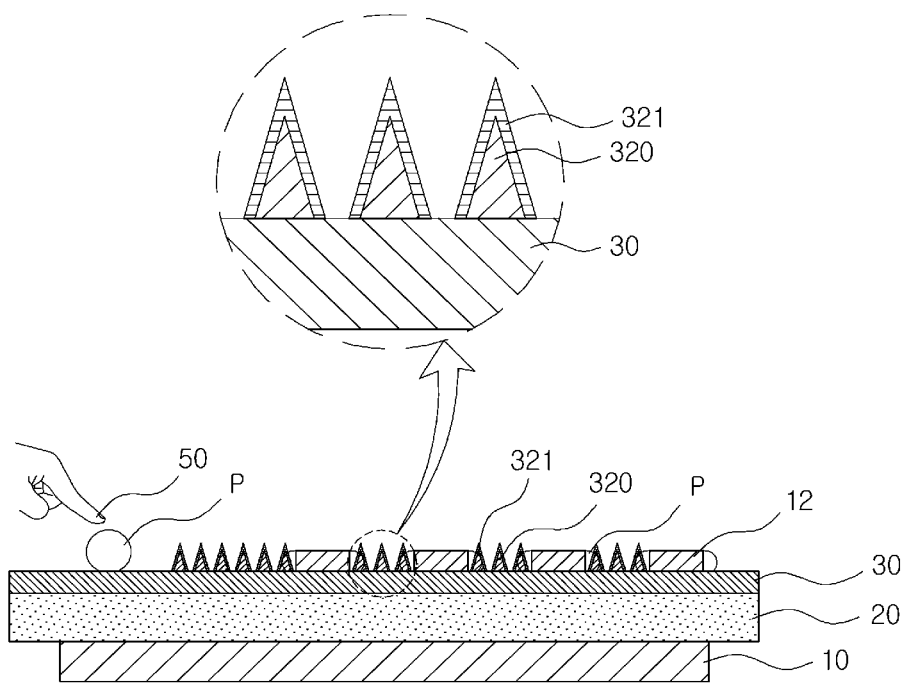
FIG. 15B is a schematic cross-sectional view illustrating the flexible active species generator in which a coating layer is formed on the fine pore-forming structure of the flexible active species generator of FIG. 15A.

FIG. 15B is a schematic cross-sectional view illustrating the flexible active species generator in which a coating layer 321 is formed on the fine pore-forming structure 320 of the flexible active species generator of FIG. 15A.

When the coating layer 321 is formed on the fine pore-forming structure 320 of the flexible active species generator as described above, the flexible active species generator contacts the skin to form fine pores in the epidermis of the organism to deliver the effective material to the dermis under the epidermis.

According to an embodiment of this disclosure, the coating layer 321 may include an effective material that is the same as or different from the effective material included in the first functional layer 30 or coated on the first functional layer 30. When the coating layer 321 includes the same effective material as the effective material included in the first functional layer 30 or coated on the first functional layer 30, a high concentration of the effective material may be delivered to the organism. On the other hand, when the coating layer 321 includes an effective material different from the effective material included in the first functional layer 30 or coated on the first functional layer 30, various effective materials may be delivered to the organism to provide complex activities.

Figure 15C:
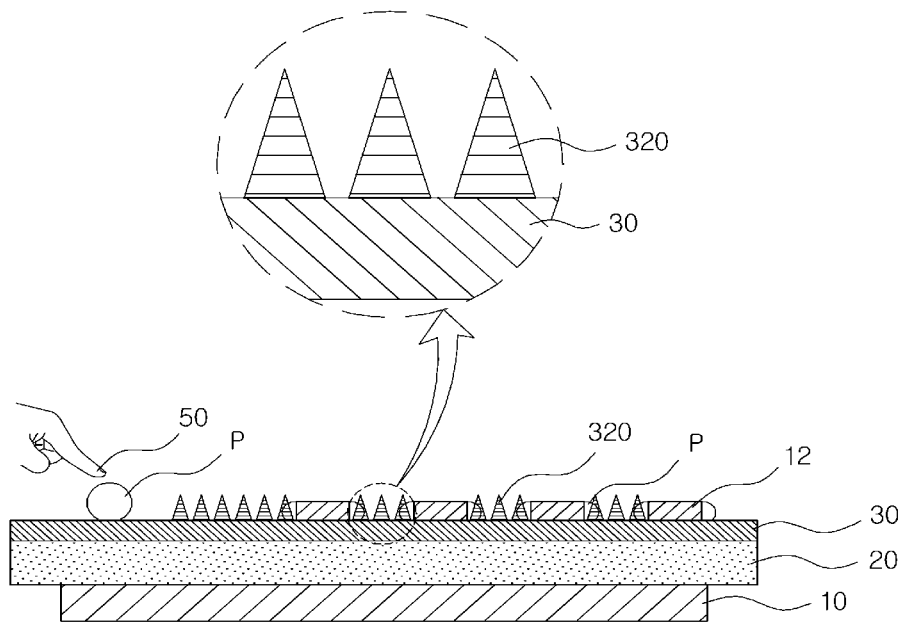
FIG. 15C is a schematic cross-sectional view illustrating the flexible active species generator in which the fine pore-forming structure of the flexible active species generator of FIG. 15A includes an effective material which is different from that of the first functional layer.

FIG. 15C is a schematic cross-sectional view illustrating the flexible active species generator in which the fine pore-forming structure 320 of the flexible active species generator of FIG. 15A includes an effective material which is different from that of the first functional layer 30.

According to an embodiment of this disclosure, the fine pore-forming structure 320 includes an effective material that is the same as or different from the effective material included in the first functional layer 30 or coated on the first functional layer 30. When the fine pore-forming structure 320 includes the same effective material as the effective material included in the first functional layer 30 or coated on the first functional layer 30, a high concentration of the effective material may be delivered to the organism. On the other hand, when the fine pore-forming structure 320 includes an effective material different from the effective material included in the first functional layer 30 or coated on the first functional layer 30, various effective materials may be delivered to the organism to provide complex activities.

Figure 16A:
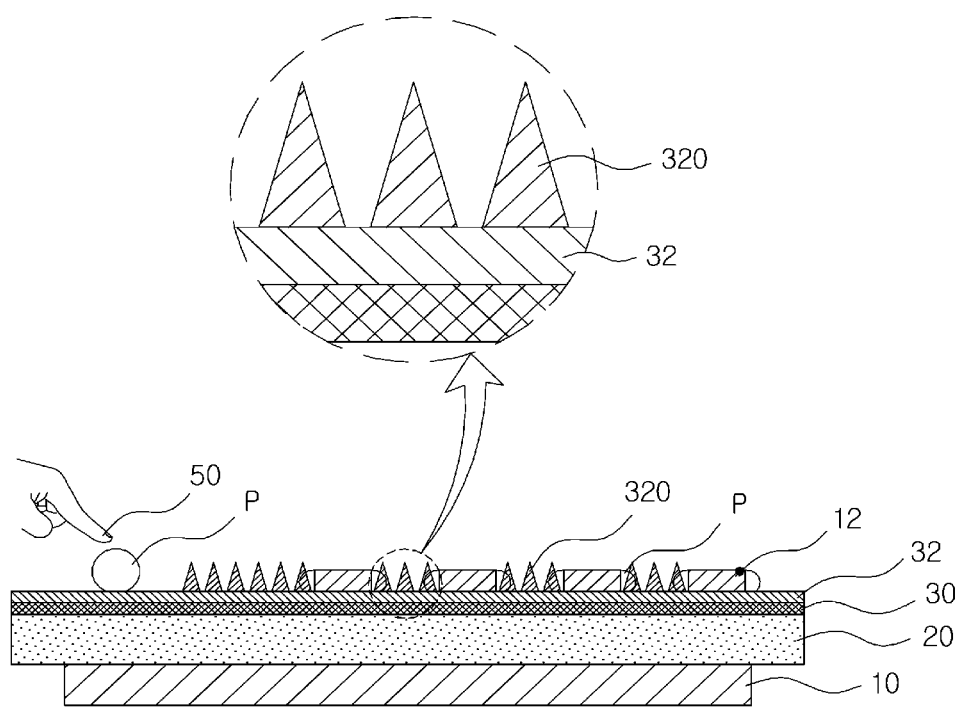
FIG. 16A is a schematic cross-sectional view illustrating a flexible active species generator according to an embodiment of this disclosure in which an effective material is included in a second functional layer and fine pore-forming structures are formed on the second functional layer.

FIG. 16A is a schematic cross-sectional view illustrating a flexible active species generator according to an embodiment of this disclosure in which an effective material is included in a second functional layer 32 and fine pore-forming structures 320 are formed on the second functional layer 32.

According to an embodiment of this disclosure, the flexible active species generator of this disclosure may include one or more functional layers, such as a second functional layer 32, on the first functional layer 30.

The flexible active species generator of FIG. 16A further includes the second electrode 12 on the first functional layer 30 as compared with the flexible active species generator of FIG. 15A. The second functional layer 32 adjacent to the second electrode 12 includes an effective material and the fine pore-forming structure 320 is formed on the second functional layer 32.

Figure 16B:
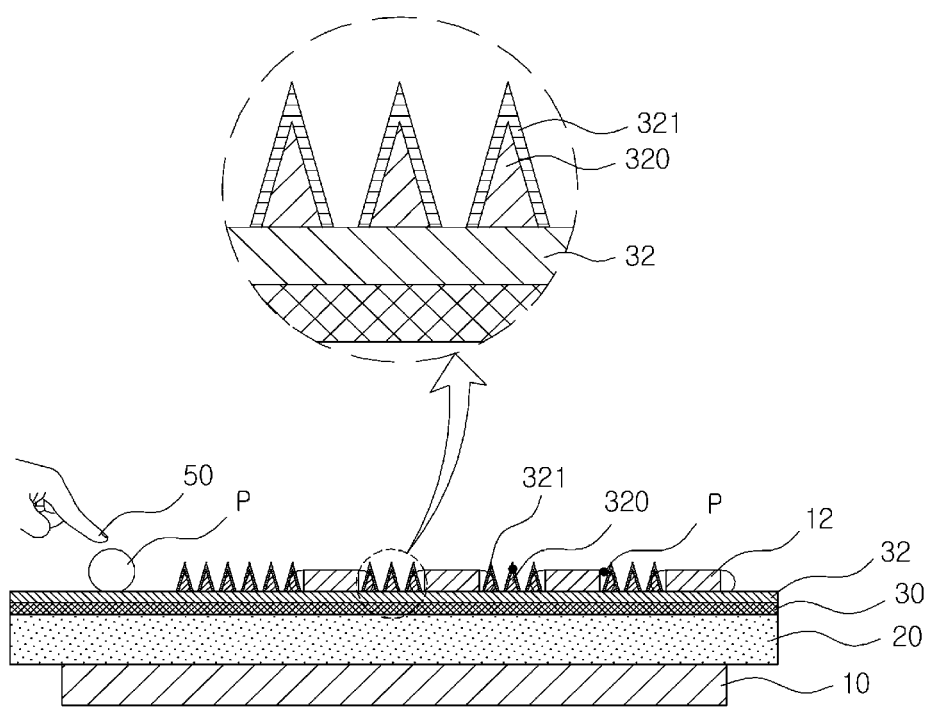
FIG. 16B is a schematic cross-sectional view illustrating the flexible active species generator in which a coating layer is formed on the fine pore-forming structure of the flexible active species generator of FIG. 16A.

FIG. 16B is a schematic cross-sectional view illustrating the flexible active species generator in which a coating layer 321 is formed on the fine pore-forming structure 320 of the flexible active species generator of FIG. 16A. The flexible active species generator of FIG. 16B further includes the second electrode 12 on the first functional layer 30 as compared with the flexible active species generator of FIG. 15B. Therefore, the structure and the function of the flexible active species generator of FIG. 16B are similar to that of FIG. 15B and detailed description thereof is omitted.

Figure 16C:
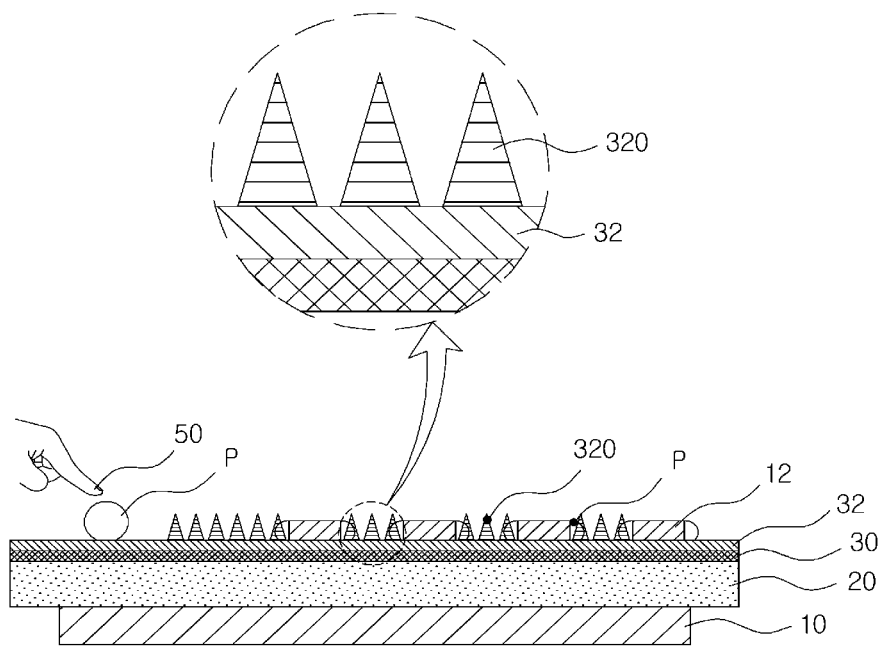
FIG. 16C is a schematic cross-sectional view illustrating the flexible active species generator in which the fine pore-forming structure of the flexible active species generator of FIG. 16A includes an effective material which is different from that of the second functional layer.

FIG. 16C is a schematic cross-sectional view illustrating the flexible active species generator in which the fine pore-forming structure 320 of the flexible active species generator of FIG. 16A includes an effective material which is different from that of the second functional layer 32. The flexible active species generator of FIG. 16C further includes the second electrode 12 on the first functional layer 30 as compared with the flexible active species generator of FIG. 15C. Therefore, the structure and the function of the flexible active species generator of FIG. 16C are similar to that of FIG. 15C and detailed description thereof is omitted.

Figure 17A:
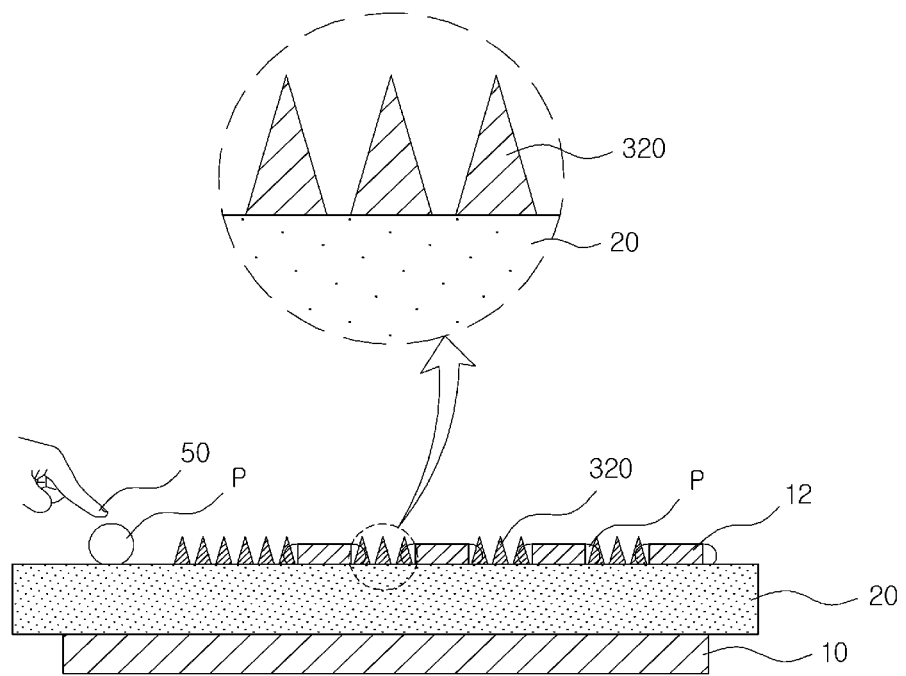
FIG. 17A is a schematic cross-sectional view illustrating a flexible active species generator according to an embodiment of this disclosure in which an effective material is included in a dielectric layer and fine pore-forming structures are formed on the dielectric layer.
Figure 17B:
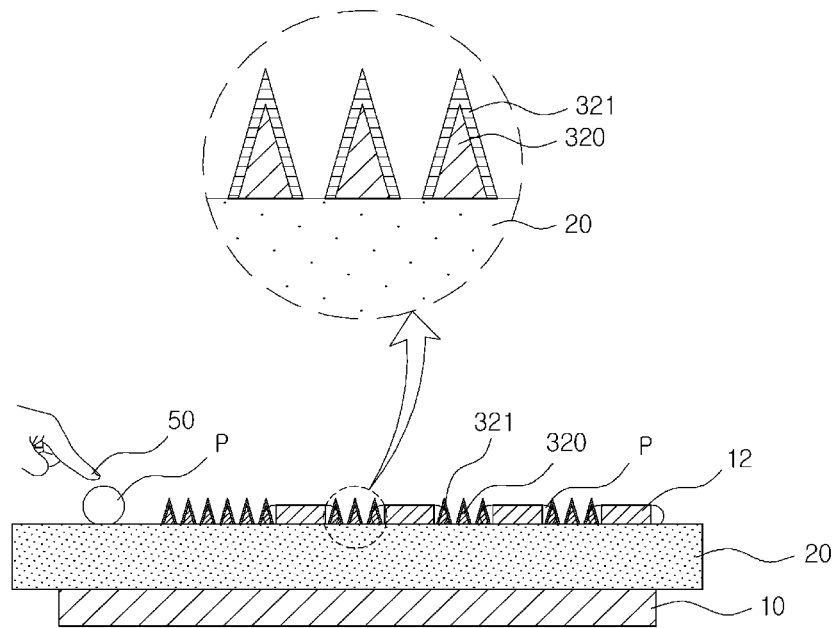
FIG. 17B is a schematic cross-sectional view illustrating the flexible active species generator in which a coating layer is formed on the fine pore-forming structure of the flexible active species generator of FIG. 17A.
Figure 17C:
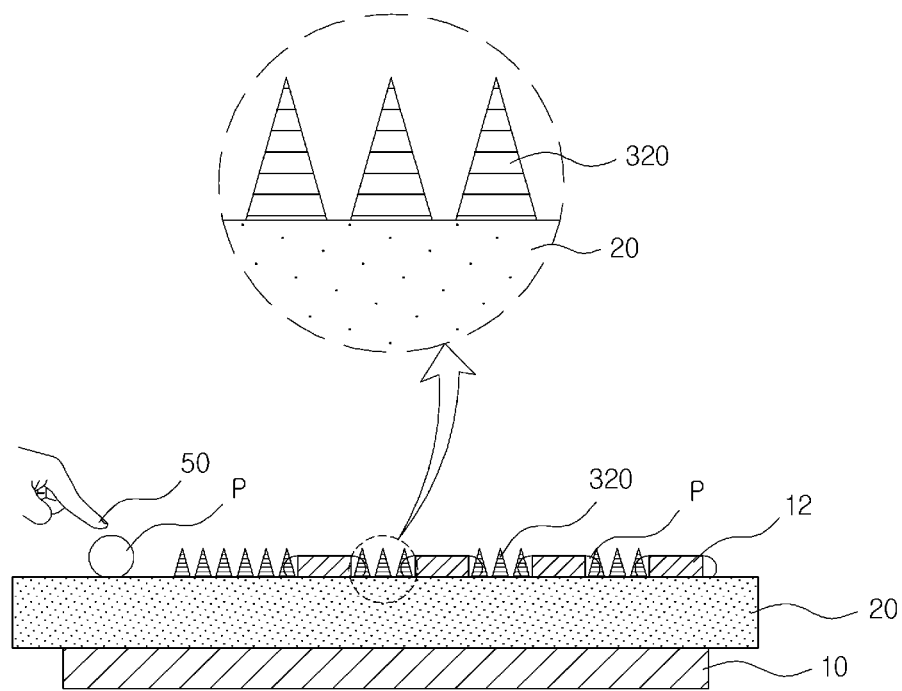
FIG. 17C is a schematic cross-sectional view illustrating the flexible active species generator in which the fine pore-forming structure of the flexible active species generator of FIG. 17A includes an effective material which is different from that of the dielectric layer.

FIG. 17A is a schematic cross-sectional view illustrating a flexible active species generator according to an embodiment of this disclosure in which an effective material is included in a dielectric layer 20 and fine pore-forming structures 320 are formed on the dielectric layer 20. FIG. 17B is a schematic cross-sectional view illustrating the flexible active species generator in which a coating layer 321 is formed on the fine pore-forming structure 320 of the flexible active species generator of FIG. 17A. FIG. 17C is a schematic cross-sectional view illustrating the flexible active species generator in which the fine pore-forming structure 320 of the flexible active species generator of FIG. 17A includes an effective material which is different from that of the dielectric layer 20.

The flexible active species generator of FIG. 17A to FIG. 17C does not include the first functional layer 30 as compared with the flexible active species generator of FIG. 15A to FIG. 15C. Therefore, the structure and the function of the flexible active species generator of FIG. 17A to FIG. 17C are similar to that of FIG. 15A to FIG. 15C and detailed description thereof is omitted.

Figure 18A:
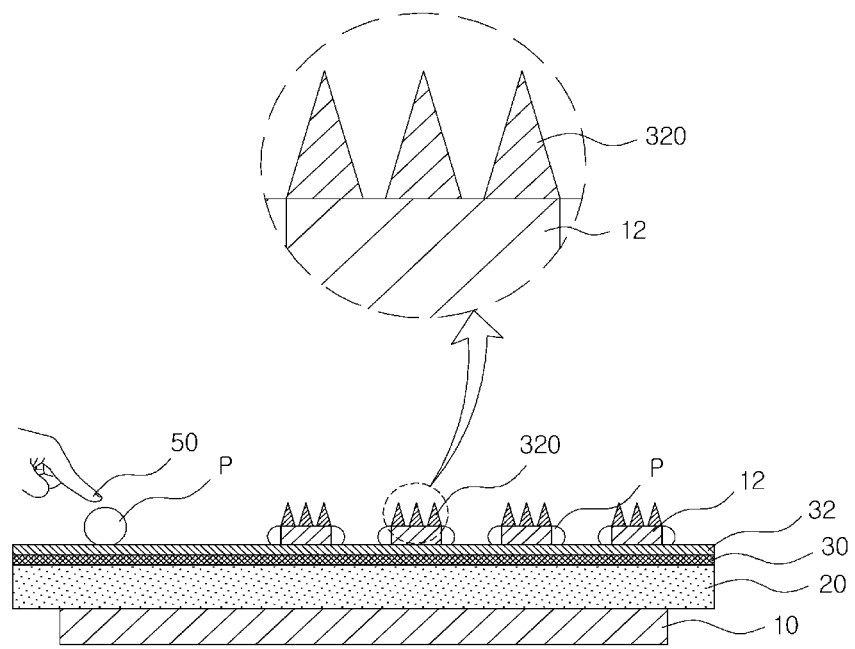
FIG. 18A is a schematic cross-sectional view illustrating a flexible active species generator according to an embodiment of this disclosure in which an effective material is included in a second electrode and fine pore-forming structures are formed on the second electrode.

FIG. 18A is a schematic cross-sectional view illustrating a flexible active species generator according to an embodiment of this disclosure in which an effective material is included in a second electrode 12 and fine pore-forming structures 320 are formed on the second electrode.

According to an embodiment of this disclosure, an effective material may be included in the second electrode 12 or coated on the second electrode 12. There is a difference in that the fine pore-forming structure 320 is formed on the second electrode 12 in the flexible active species generator of FIG. 18 as compared with the flexible active species generator of FIG. 16A. Thus, even when the height of the fine pore-forming structure 320 is low, the flexible active species generator can easily form fine pores in the epidermis of an organism when it comes into contact with the skin.

Figure 18B:
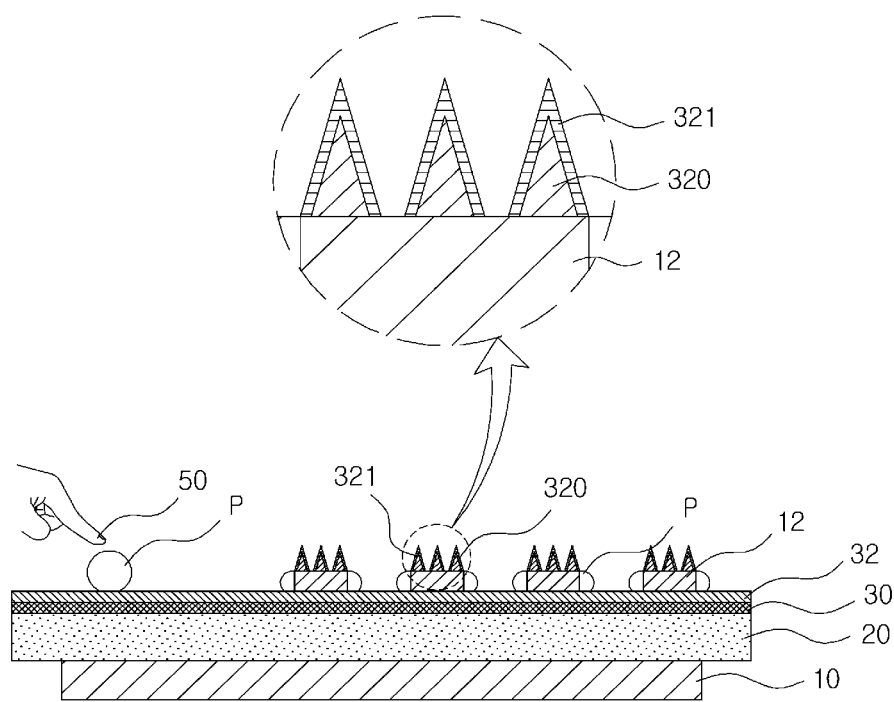
FIG. 18B is a schematic cross-sectional view illustrating the flexible active species generator in which a coating layer is formed on the fine pore-forming structure of the flexible active species generator of FIG. 18A.
Figure 18C:
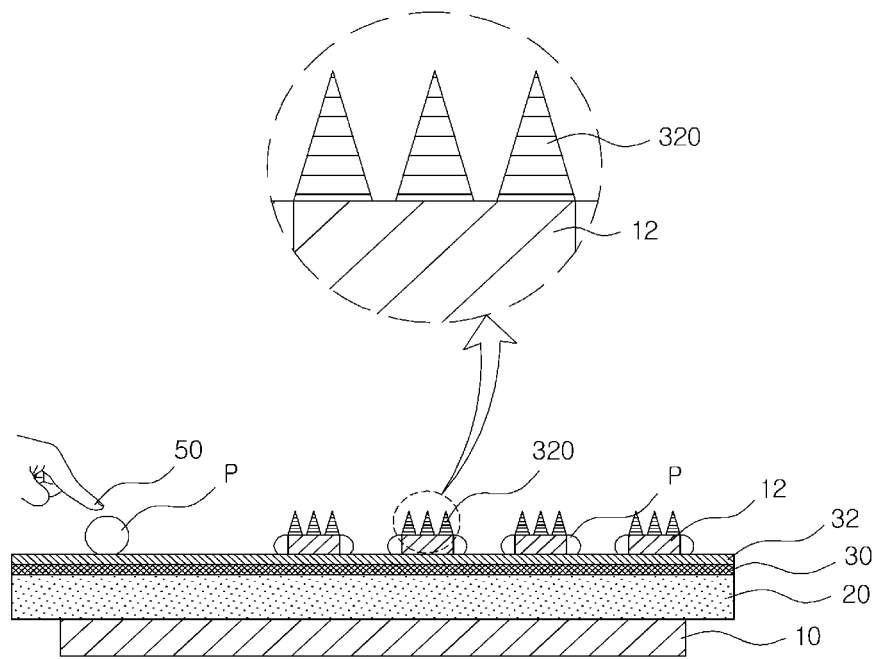
FIG. 18C is a schematic cross-sectional view illustrating the flexible active species generator in which the fine pore-forming structure of the flexible active species generator of FIG. 18A includes an effective material which is different from that of the second electrode.

FIG. 18B is a schematic cross-sectional view illustrating the flexible active species generator in which a coating layer 321 is formed on the fine pore-forming structure 320 of the flexible active species generator of FIG. 18A. FIG. 18C is a schematic cross-sectional view illustrating the flexible active species generator in which the fine pore-forming structure 320 of the flexible active species generator of FIG. 18A includes an effective material which is different from that of the second electrode 12. There is a difference in that the fine pore-forming structure 320 is formed on the second electrode 12 in the flexible active species generator of FIG. 18B and FIG. 18C as compared with the flexible active species generator of FIG. 16B and FIG. 16C. Therefore, the structure and the function of the flexible active species generator of FIG. 18B and FIG. 18C are similar to that of FIG. 16B and FIG. 16C and detailed description thereof is omitted.

Hereinafter, the effect of the flexible seed generator according to this disclosure will be described in detail in the following examples.

EXAMPLE 1

Preparation of a Flexible Active Species Generator with a Plasma Resistant Thin Film FIG. 1 is a cross-sectional view illustrating a flexible active species generator 100 according to an embodiment of this disclosure. As shown in FIG. 1, a first electrode 10 of an electric field providing electrode, a first and a second insulating films (PET) of a dielectric layer 20, a functional layer having a plasma resistance 30 ($SiO_x$), and a second electrode 12 of a ground electrode were laminated.

COMPARATIVE EXAMPLE 1

Preparation of a Flexible Active Species Generator with a Plasma Resistant Thin Film A first electrode of an electric field providing electrode, a first and a second insulating films (PET) of a dielectric layer, and a second electrode of a ground electrode were laminated.

Each of the flexible active species generators of Example 1 and Comparative Example 1 was operated at the same conditions of a voltage of 2 kV, a sine wave frequency of 20 kHz.

Result

Figure 5:
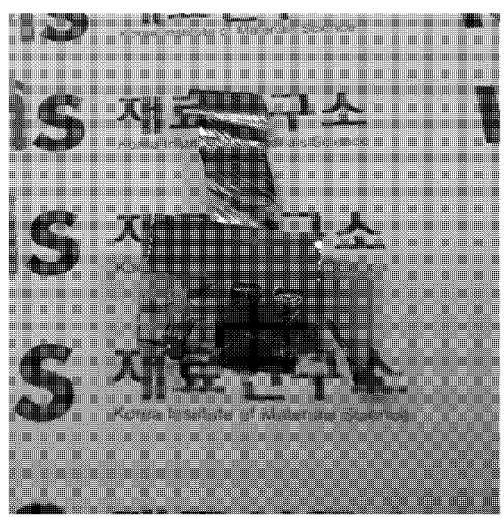
FIG. 5 illustrates results of preventing deformation and decomposition of an insulator by a plasma resistant functional layer according to an embodiment of this disclosure, in which the left image is an active species generator without a plasma resistant functional layer and the right image is that with a plasma resistant functional layer.
Figure 5:
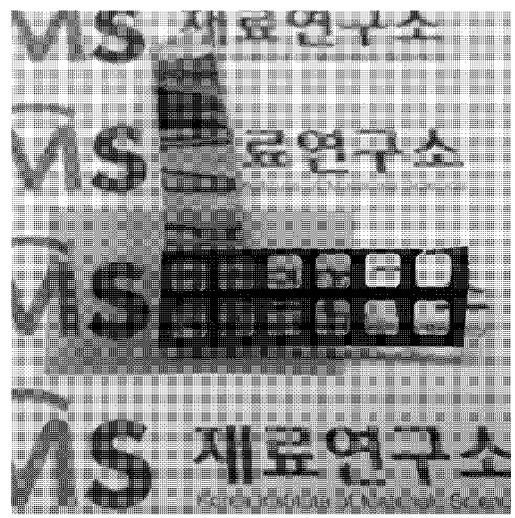

In case of Comparative Example 1, a discharger was thermally damaged by the deformation of the insulating film PET about 2 minutes after continuous discharge as shown the right image of FIG. 5. On the other hand, in the case of Example 1, the PET was not damaged even about 5 minutes after continuous discharge, and the plasma discharge was stably performed. Through this, it was confirmed that the operational stability of the flexible active species generator was improved by coating with the oxide compound.

Figure 4:
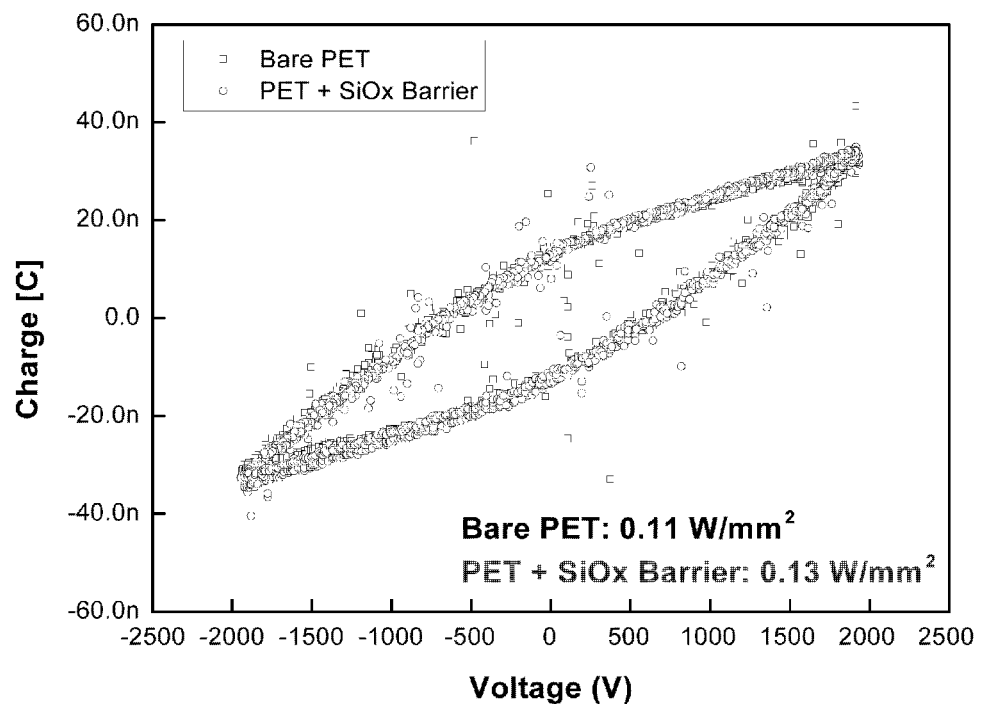
FIG. 4 is a Q-V lissajous diagram illustrating discharge power consumption of a flexible active species generator with a plasma resistant functional layer according to an embodiment of this disclosure, and that of a flexible active species generator without a plasma resistant functional layer.

As shown in FIG. 4, the Q-V Lissajous diagram confirms the power consumed during discharge. The Q-V Lissajous plot is a method to determine the power consumed in a dielectric barrier discharge (DBD), which calculates the amount of charge stored in a discharger based on an applied voltage. Parallelogram shape graphs can be obtained through this method, and the area of the parallelogram corresponds to the power consumed in one cycle of AC voltage.

According to the Q-V Lissajous plot, the discharge power consumption of Comparative Example 1 was 0.11 W/mm$^2$, but that of Example 1 of this disclosure was 0.13 W/mm$^2$. In general, as a generation amount of active species increases proportionally to the discharge power consumption, it shows that the generation amount of active species per unit area in Example 1 is 15% more compared to that in Comparative Example 1 (see FIG. 3 and FIG. 4).

EXAMPLE 2

Preparation of a Flexible Active Species Generator Coated with a Secondary Electron-Generating Oxide As shown in FIG. 6, a first electrode 10 of an electric field providing electrode, a first and a second insulating films (PET) of a dielectric layer 20, a plasma resistant first functional layer 30 (SiO$_x$) including a secondary electron generating compound (MgO)-coating layer 32, and a second electrode of a ground electrode were laminated.

COMPARATIVE EXAMPLE 2

Preparation of a Flexible Active Species Generator Coated with a Secondary Electron-Generating Oxide A first electrode of an electric field providing electrode, a first and a second insulating films (PET) of a dielectric layer, and a second electrode of a ground electrode were laminated.

Each of the flexible active species generators of Example 2 and Comparative Example 2 was operated at the same conditions of a voltage of 2 kV, a sine wave frequency of 20 kHz.

Result

Figure 7:
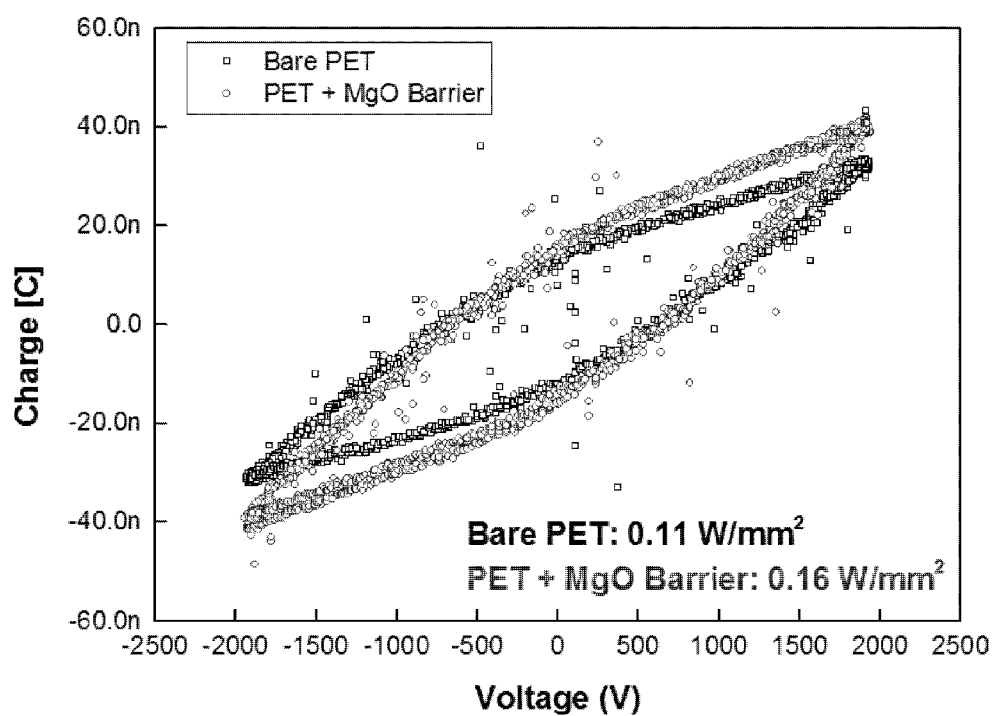
FIG. 7 is a Q-V lissajous diagram illustrating discharge power consumption of a flexible active species generator coated with a secondary electron-generating oxide on a functional layer according to an embodiment of this disclosure, and that of a flexible active species generator not coated with a secondary electron-generating oxide on a functional layer.

As shown in FIG. 7, the discharge power consumption of Comparative Example 2 determined by the Q-V Lissajous plot was 0.11 W/mm$^2$, but that of Example 2 of this disclosure was 0.16 W/mm$^2$. As a generation amount of active species increases proportionally to the discharge power consumption, it shows that the generation amount of active species per unit area in Example w is 45% more compared to that in Comparative Example 2 (see FIG. 6 and FIG. 7). It was also confirmed that the charge generation amount increased by about 30% or more at the same discharge voltage (2 kV). It was also confirmed that coating the top part of the functional layer with a compound having a high secondary electron generation coefficient reduced the discharge voltage of the flexible active species generator.

Figure 8:
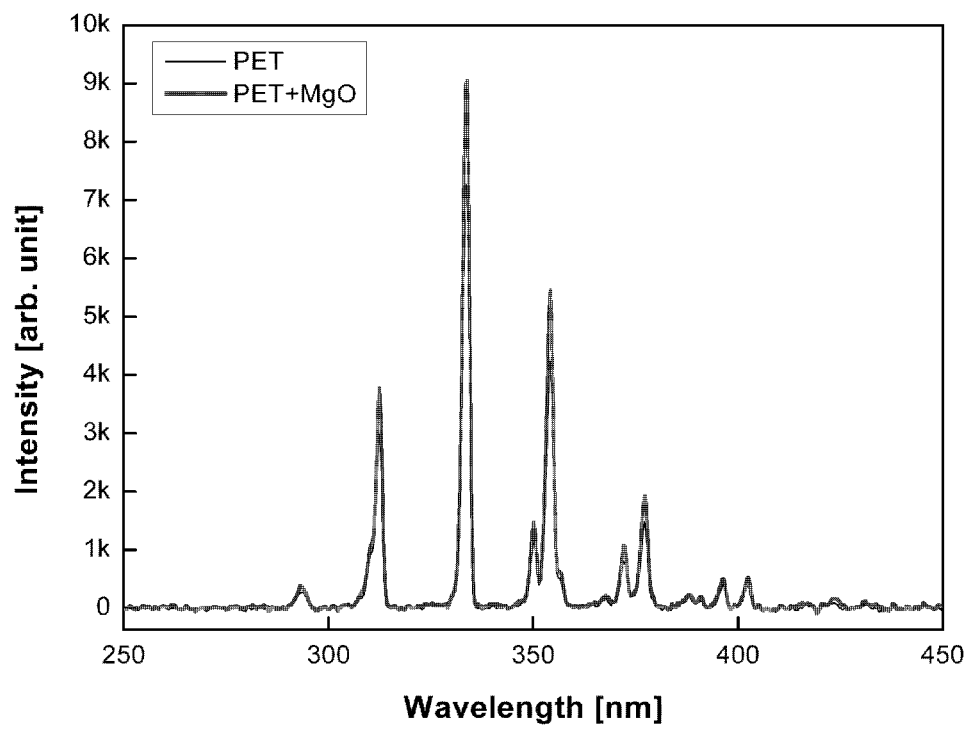
FIG. 8 is an emission spectrum graph of active species generating plasma illustrating intensity of active species generation of a flexible active species generator according to an embodiment of this disclosure.

According to FIG. 8 illustrating an emission spectrum from the nitrogen active species excited by collision between electrons generated from the active species generator and nitrogen in the air, intensity of active species generation of the flexible active species generator coated with the secondary electron generating compound-coating layer in Example 2 was greater than that of the flexible active species generator not coated with the secondary electron generating compound-coating layer in Comparative Example 2. Thus, it was confirmed that generation of active species of Example 2 is greater than that of Comparative Example 2.

EXAMPLE 3

Preparation of a Flexible Active Species Generator with Blood Coagulation Function As shown in FIG. 9, a first electrode 10 of an electric field providing electrode, a first insulating film (PET) of dielectric layers 22, 24, and a second electrode 14 (porous Ni) having a thickness of 3 mm of a ground electrode were laminated. The active species generated from the gap between the dielectric layer and the second electrode comes out through the porous second electrode.

COMPARATIVE EXAMPLE 3

Preparation of a Flexible Active Species Generator with Blood Coagulation Function A first electrode of an electric field providing electrode, a first and a second insulating films (PET) of a dielectric layer, and a second electrode of a ground electrode were laminated.

Each of the flexible active species generators of Example 3 and Comparative Example 3 was operated at the same conditions of a voltage of 1.7 kV, a sine wave frequency of 20 kHz. This experiment was to compare the smooth operation of the active species generator even when it is contacted with blood, not the evaluation of the active species generation performance in the same area.

Result

Figure 12:
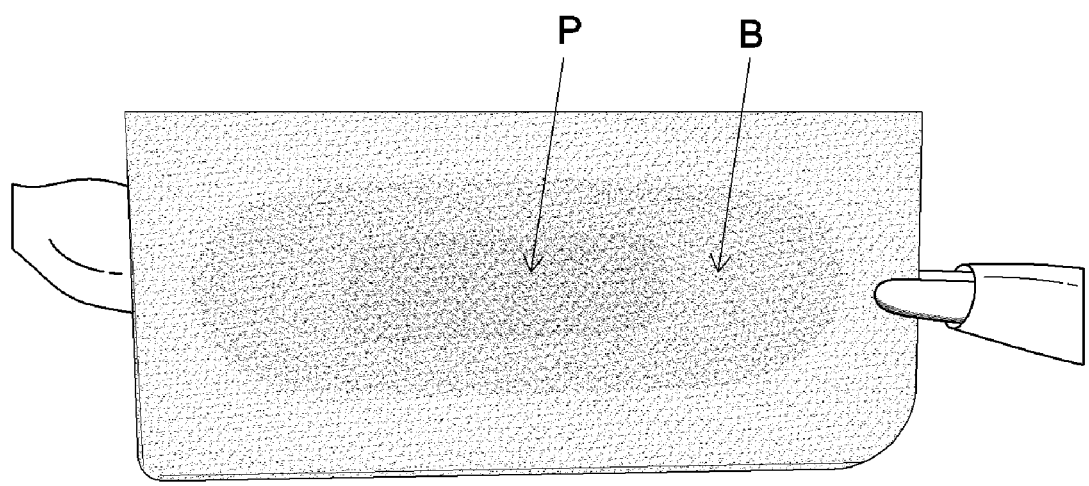
FIG. 12 is an image illustrating that plasma is formed in the fine gap between a second electrode and a dielectric layer of a flexible active species generator having a porous second electrode according to an embodiment of this disclosure.

As shown in FIG. 10 illustrating the Q-V Lissajous diagram comparing discharge power consumption, the total discharge power consumption of the flexible active species generator of Comparative Example 3 before the blood contact was 2.08 W, while that after blood contact was reduced to 1.02 W. This is because the blood was filled the gap for generating the active species and the discharge did not occur. According to FIG. 11, it is noted that there is no discharge due to the blood B filled in the gap where the plasma P is to be formed for generating active species. However, as shown in FIG. 12 where the porous material is applied to the second electrode 12, plasma P is formed in the micro gap between the second electrode and the dielectric layer and blood B is not directly contacted on the surface where the plasma P is generated due to the structure of the porous second electrode, so that active species is smoothly generated.

In addition, if the dielectric layer is formed of Teflon having water repellency and blood repellency, or if it is formed of a blood repellent surface composed of a dielectric layer and a functional layer, the blood flowing through the porous second electrode can more effectively prevent the filling of the gap.

Figure 13:
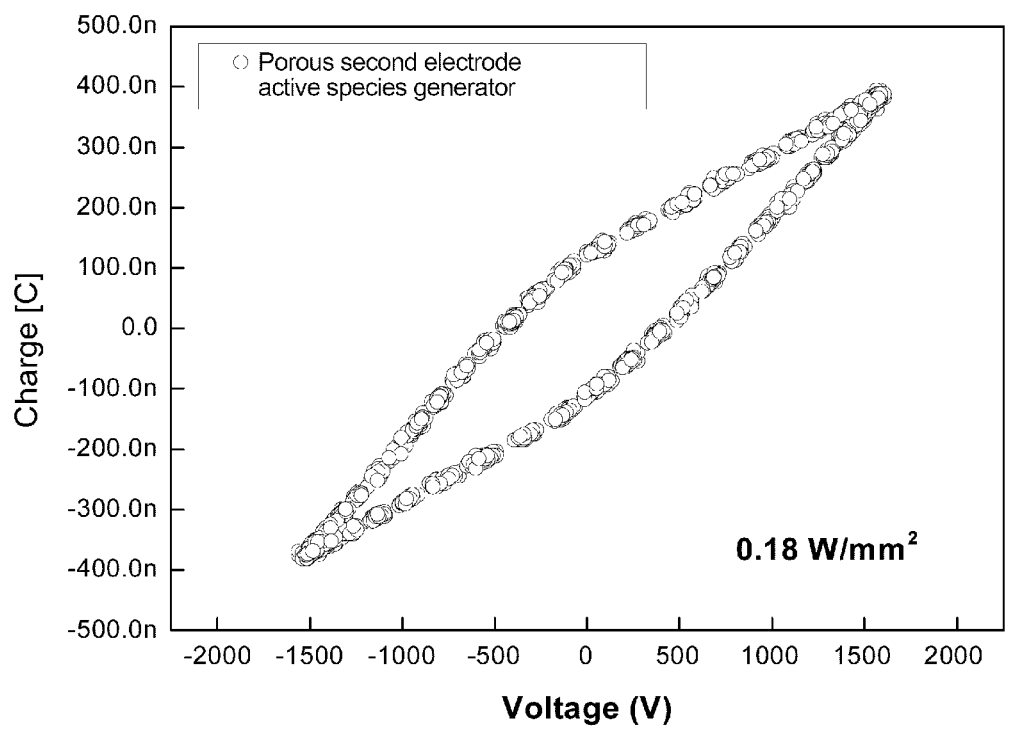
FIG. 13 is a Q-V lissajous diagram illustrating discharge power consumption of a flexible active species generator having a porous second electrode according to an embodiment of this disclosure.
Figure 14:
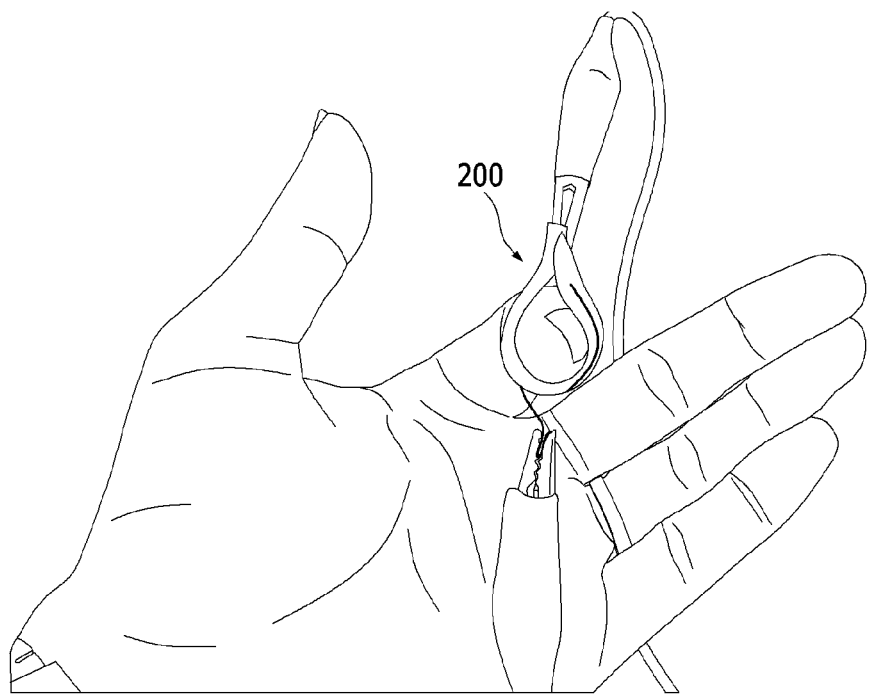
FIG. 14 is an image illustrating that a flexible active species generator having a flexible porous second electrode according to an embodiment of this disclosure may be safely used as a hemostatic band in the human body.

In addition, since the porous second electrode has a larger area available for discharge than the lattice-shaped second electrode, the discharge power consumption was 0.18 W/mm$^2$ as shown in FIG. 13. This means that more active species can be generated per unit area. When a flexible porous second electrode is applied, as shown in FIG. 14, it is possible to provide an active species generator in a band form and the second electrode is electrically grounded, so that the electric stability can be secured easily when the electrode is used in the human body.

DESCRIPTION OF REFERENCE NUMERALS

10: First electrode
12, 14: Second electrodes
20, 22, 24: Dielectric layers
30: First functional layer
32: Second functional layer
50: human body
100, 200: Flexible active species generators
320: Fine pore-forming structure
321: Effective material coating layer
P: Plasma
R: Active species
B: Blood

What is claimed is:

1. An active species generator comprising:
    a first electrode of a conductive metal film;
    a second electrode of a ground electrode;
    a flexible dielectric layer of an insulator formed between the first electrode and the second electrode; and
    a plasma resistant functional layer formed between the dielectric layer and the second electrode, wherein the first electrode and the second electrode are electrically connected to an external power supply to generate an atmospheric pressure plasma to generate active species,
    wherein at least one of the dielectric layer and the plasma resistant functional layer includes an effective material, and
    wherein the effective material provides at least one effect selected from a cosmetic effect, an antibacterial effect, an anticancer effect, and an antiviral effect,
    wherein the effective material is at least one selected from the group consisting of a plant extract, a physiologically active material, an anticancer agent, and a vaccine,
    wherein the physiologically active material is at least one selected from caffeic acid, anomalin, adonitol, flavonoid, saponin, rutin, glutamic acid, quercetin, and astaxanthin,
    wherein the functional layer prevents physical or chemical changes in the dielectric layer, and
    wherein the functional layer is coated with an oxide that generates secondary electrons to reduce discharge voltage.

2. The active species generator of claim 1, wherein the functional layer is formed of one selected from the group consisting of Al2O3, SiOx, SiOxCyHz, a-C and a-C:H.

3. The active species generator of claim 1, wherein the second electrode is formed in a lattice or porous form.

4. The active species generator of claim 1, wherein the dielectric layer is formed of one selected from the group consisting of polymer, flexible glass, fabric and paper.

5. The active species generator of claim 1, wherein the functional layer further comprises a self-cleaning layer, a super water-repellent layer, a light-emitting layer or a mixed layer thereof.

6. The active species generator of claim 1, wherein at least one of the first electrode and the second electrode is formed of a flexible conductive material.

7. The active species generator of claim 1, wherein the second electrode is formed of a porous conductive material, a fabric conductive material, or a combination thereof.

8. The active species generator of claim 1, wherein at least one of the first electrode and the second electrode is formed of a transparent conductive material.

9. The active species generator of claim 1, wherein the dielectric layer is formed of one selected from the group consisting of polyethylene terephthalate, polyimide, polycarbonate, polyethylene, polyurethane, poly-methyl methacrylate, polystyrene, polytetrafluoroethylene, polydimethylsiloxane, and a mixture thereof.

10. The active species generator of claim 1, wherein the dielectric layer comprises:
    a first dielectric layer formed on the bottom part and the side parts of the first electrode; and
    a second dielectric layer formed on the upper part of the first electrode.

11. The active species generator of claim 1, wherein the at least one selected from the second electrode and the plasma resistant functional layer comprising the effective material is formed of a flexible conductive material.

12. The active species generator of claim 1, wherein the dielectric layer comprises the effective material and is formed of a flexible non-conductive material.

13. The active species generator of claim 7, further comprising a plurality of fine pore-forming structures formed on the second electrode or on the functional layer in contact with the second electrode to form fine pores in the epidermis of an organism.

* * * * *